(12) United States Patent
Michaels

(10) Patent No.: US 8,758,759 B2
(45) Date of Patent: Jun. 24, 2014

(54) TRANSMUCOSAL ADMINISTRATION OF AGGREGATED ANTIGENS

(75) Inventors: Frank Michaels, Havertown, PA (US); Karen Dohm, legal representative, Havertown, PA (US)

(73) Assignee: Enzo Biochem, Inc., Farmingdale, NY (US)

( * ) Notice: Subject to any disclaimer, the term of this patent is extended or adjusted under 35 U.S.C. 154(b) by 2472 days.

(21) Appl. No.: 10/531,805

(22) PCT Filed: Oct. 17, 2003

(86) PCT No.: PCT/US03/33178
§ 371 (c)(1), (2), (4) Date: Jan. 28, 2008

(87) PCT Pub. No.: WO2004/035007
PCT Pub. Date: Apr. 29, 2004

(65) Prior Publication Data
US 2011/0097362 A1    Apr. 28, 2011

Related U.S. Application Data

(60) Provisional application No. 60/419,279, filed on Oct. 17, 2002.

(51) Int. Cl.
*A61K 39/00* (2006.01)

(52) U.S. Cl.
USPC ................... 424/184.1; 424/278.1; 424/190.1

(58) Field of Classification Search
None
See application file for complete search history.

(56) References Cited

U.S. PATENT DOCUMENTS 6,355,248 B1    3/2002   Michaels et al.

FOREIGN PATENT DOCUMENTS

| EP | 1 136 077 A1 | 9/2001 |
| EP | 1 149 586 A1 | 10/2001 |

OTHER PUBLICATIONS

Hunneyball et al., Immunology, 1979, vol. 37, p. 529-537.*
Safadi, et al., "Oral Immune-Regulation towards Hepatitis B Virus Proteins a New Mode of Treatment for Chronic HBV Infection: Results of a Phase I Clinical Trial", Hepatology, vol. 32, No. 4, Part 2, p. 379A, 2000.
Safadi, et al., "Treatment of Chronic Hepeatitis B Virus Infection via Oral Immune Regulation toward Hepatitis B Virus Proteins", American Journal of Gastroenterology, vol. 98, No. 11, pp. 2505-2515, Nov. 2003.
Gotsman, et al., "Induction of Oral Tolerance towards Hepatitis B Envelope Antigens in a Murine Model", vol. 48, No. 1, pp. 17-26, 2000.
Shouval et al., "Improved Immunogenicity in Mice of a Mammalian Cell-derived Recombinant Hepatitis B Vaccine Containing Pre-S1 and Pre-S2 antigens as compared with conventional yeast-derived Vaccines", Vaccine, vol. 12, No. 15, pp. 1453-1459, Nov. 1994.
Childers et al., "Mucosal and Systemic Responses to an Oral Liposome-*Streptococcus mutans* Carbohydrate Vaccine in Humans", Regional Immunology, vol. 3, No. 6, pp. 289-296, 1990.
Van der Lubben et al., "Chitosan for Mucosal Vaccination", Advanced Drug Delivery Reviews, vol. 52, No. 2, pp. 139-144, 2001.
"Oral Viral Proteins" B Informed; The Newsletter of the Hepatitis B Foundation, No. 29, pp. 4-5, 2000.
Mcsorley et al., "Vaccination by inducing oral Tolerence?", Immunology Today 1999 United Kingdom, vol. 20, No. 12, pp. 555-560, 1999.
Weiner, "Oral Tolerence: Immune Mechanisms and Treatment of Autoimmune Diseases", Immunology Today, vol. 19, No. 7, pp. 335-343, Jul. 1997.
Youhai Chen, et al., "Peripheral Deletion of Antigen-reactive T Cells in Oral Tolerance" Nature, vol. 376, No. 6536, pp. 177-180, Jul. 13, 1995.
Youhai Chen, et al., "Regulatory T Cell Clones Induced by Oral Tolerance: Suppression of Autoimmune Encephalomyelitis" Science, vol. 265, 1237-1240, Aug. 26, 1994.
Eyal Klipper, et al., "Response, Tolerance and Ignorance Following Oral Exposure to a Single Dietary Protein Antigen in Gallus domesticus" Vaccine, vol. 19, pp. 2890-2897, 2001.
Ulf Schröder, et al., "Nasal and Parenteral Immunizations with Diphtheria Toxoid Using Monoglyceride/fatty acid Lipid Suspensions as Adjuvants" Vaccine, vol. 17, pp. 2096-2103, 1999.
Elizabeth J. Ryan, et al., "Immunomodulators and Delivery Systems for Vaccination by Mucosal Routes" Trends in Biotechnology, vol. 19, No. 8, pp. 293-304, Aug. 2001.

* cited by examiner

*Primary Examiner* — Yunsoo Kim
(74) *Attorney, Agent, or Firm* — Anna D. DiGabriele Petti, Esq.

(57) ABSTRACT

The present invention relates to modulation of the immune response in a mammal. In particular, the invention relates to methods of inducing oral tolerance and systemic immunity in a mammal. The invention sets forth methods and compositions useful in inducing oral tolerance and systemic immunity in a mammal.

22 Claims, 9 Drawing Sheets

```
       TAGGCATAAATTGGTCTGCGCACCAGCACCATGCAACTTTTTCACCTCTGCCTAATCATC
     1 ---------+---------+---------+---------+---------+---------+  60
       ATCCGTATTTAACCAGACGCGTGGTCGTGGTACGTTGAAAAAGTGGAGACGGATTAGTAG
a        *  A  *  I  G  L  R  T  S  T  M  Q  L  F  H  L  C  L  I  I   -
       TCTTGTTCATGTCCTACTGTTCAAGCCTCCAAGCTGTGCCTTGGGTGGCTTTGGGGCATG
    61 ---------+---------+---------+---------+---------+---------+ 120
       AGAACAAGTACAGGATGACAAGTTCGGAGGTTCGACACGGAACCCACCGAAACCCCGTAC
a        S  C  S  C  P  T  V  Q  A  S  K  L  C  L  G  W  L  W  G  M   -
       GACATCGACCCTTATAAAGAATTTGGAGCTACTGTGGAGTTACTCTCGTTTTTGCCTTCT
   121 ---------+---------+---------+---------+---------+---------+ 180
       CTGTAGCTGGGAATATTTCTTAAACCTCGATGACACCTCAATGAGAGCAAAAACGGAAGA
a        D  I  D  P  Y  K  E  F  G  A  T  V  E  L  L  S  F  L  P  S   -
       GACTTCTTTCCTTCAGTACGAGATCTTCTAGATACCGCCTCAGCTCTGTATCGGGAAGCC
   181 ---------+---------+---------+---------+---------+---------+ 240
       CTGAAGAAAGGAAGTCATGCTCTAGAAGATCTATGGCGGAGTCGAGACATAGCCCTTCGG
a        D  F  F  P  S  V  R  D  L  L  D  T  A  S  A  L  Y  R  E  A   *_"
       TTAGAGTCTCCTGAGCATTGTTCACCTCACCATACTGCACTCAGGCAAGCAATTCTTTGC
   241 ---------+---------+---------+---------+---------+---------+ 300
       AATCTCAGAGGACTCGTAACAAGTGGAGTGGTATGACGTGAGTCCGTTCGTTAAGAAACG
a        L  E  S  P  E  H  C  S  P  H  H  T  A  L  R  Q  A  I  L  C   -
       TGGGGGGAACTAATGACTCTAGCTACCTGGGTGGGTGTTAATTTGGAAGATCCAGCGTCT
   301 ---------+---------+---------+---------+---------+---------+ 360
       ACCCCCCTTGATTACTGAGATCGATGGACCCACCCACAATTAAACCTTCTAGGTCGCAGA
a        W  G  E  L  M  T  L  A  T  W  V  G  V  N  L  E  D  P  A  S   -
       AGAGACCTAGTAGTCAGTTATGTCAACACTAATATGGGCCTAAAGTTCAGGCAACTCTTG
   361 ---------+---------+---------+---------+---------+---------+ 420
       TCTCTGGATCATCAGTCAATACAGTTGTGATTATACCCGGATTTCAAGTCCGTTGAGAAC
a        R  D  L  V  V  S  Y  V  N  T  N  M  G  L  K  F  R  Q  L  L   -
       TGGTTTCACATTTCTTGTCTCACTTTTGGAAGAGAAACAGTTATAGAGTATTTGGTGTCT
   421 ---------+---------+---------+---------+---------+---------+ 480
       ACCAAAGTGTAAAGAACAGAGTGAAAACCTTCTCTTTGTCAATATCTCATAAACCACAGA
a        W  F  H  I  S  C  L  T  F  G  R  E  T  V  I  E  Y  L  V  S   -
       TTCGGAGTGTGGATTCGCACTCCTCCAGCTTATAGACCACCAAATGCCCCTATCCTATCA
   481 ---------+---------+---------+---------+---------+---------+ 540
       AAGCCTCACACCTAAGCGTGAGGAGGTCGAATATCTGGTGGTTTACGGGGATAGGATAGT
a        F  G  V  W  I  R  T  P  P  A  Y  R  P  P  N  A  P  I  L  S   -
       ACACTTCCGGAGACTACTGTTGTTAGACGACGAGGCAGGTCCCCTAGAAGAAGAACTCCC
   541 ---------+---------+---------+---------+---------+---------+ 600
       TGTGAAGGCCTCTGATGACAACAATCTGCTGCTCCGTCCAGGGGATCTTCTTCTTGAGGG
a        T  L  P  E  T  T  V  V  R  R  R  G  R  S  P  R  R  R  T  P   -
       TCGCCTCGCAGACGAAGGTCTCAATCGCCGCGTCGCAGAAGATCTCAATCTCGGGAATCT
   601 ---------+---------+---------+---------+---------+---------+ 660
       AGCGGAGCGTCTGCTTCCAGAGTTAGCGGCGCAGCGTCTTCTAGAGTTAGAGCCCTTAGA
a        S  P  R  R  R  R  S  Q  S  P  R  R  R  R  S  Q  S  R  E  S   -
       CAATGTTAG
   661 --------- 669
       GTTACAATC
a        Q  C  *   -

Enzymes that do cut:
NONE
```

FIGURE 1

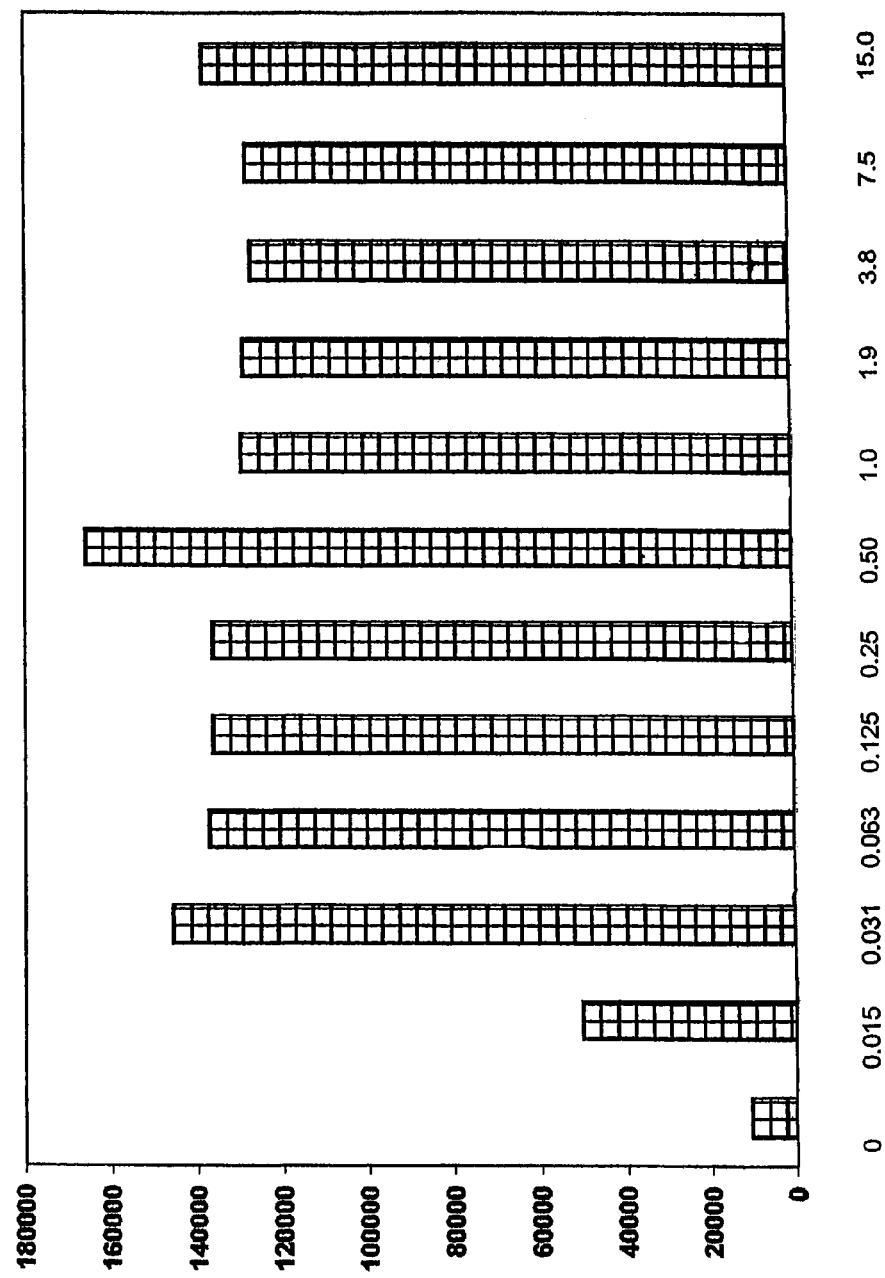

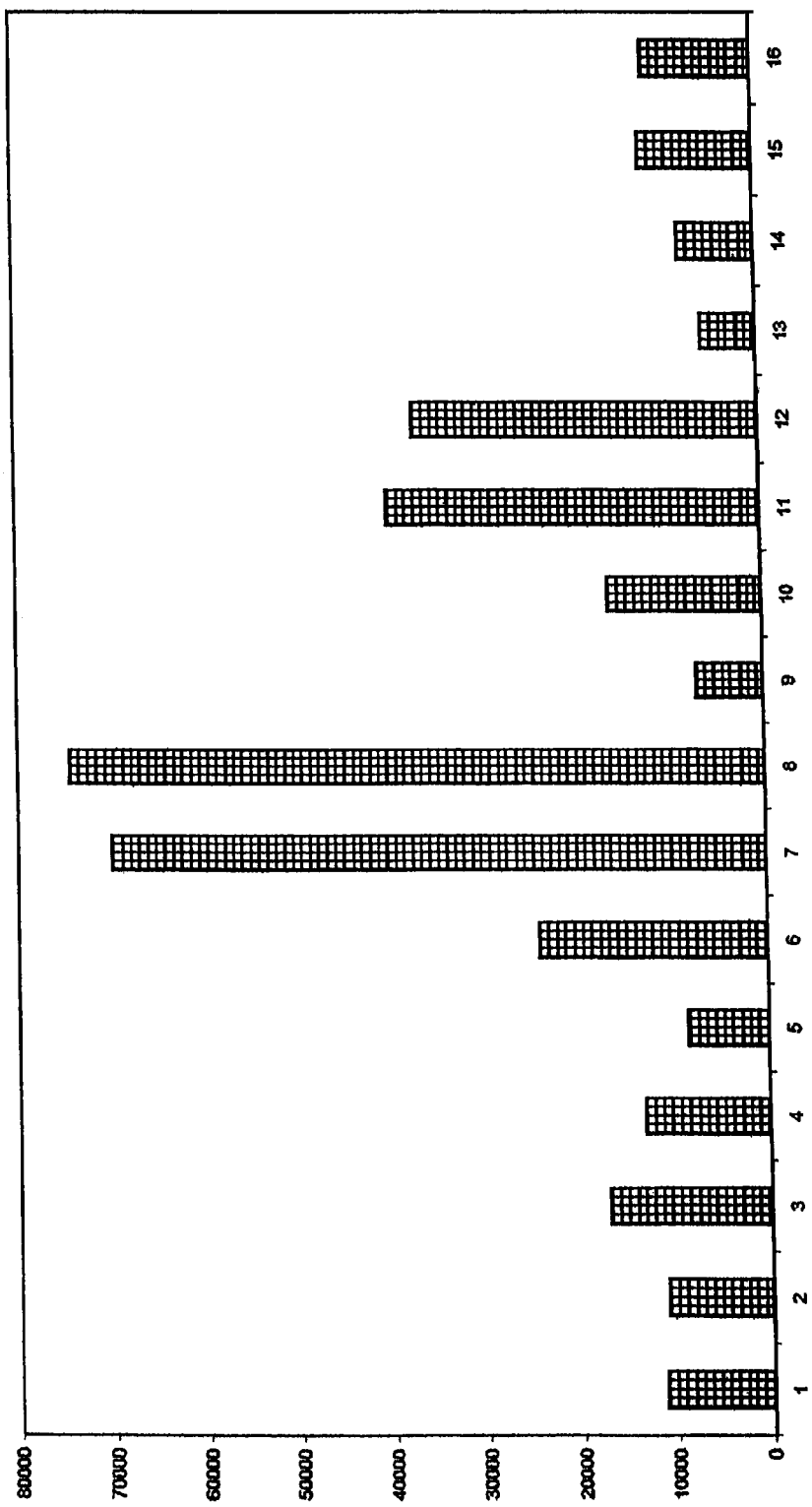

Figure 4b

| Treatment | day 2 | day 3 |
|---|---|---|
| Imm no ag | 5096 | 11224 |
| Imm 0.1 ug | 5614 | 10904 |
| Imm 1 ug | 7266 | 16991 |
| Imm 5 ug | 5882 | 13120 |
| Imm OT (3mg) no ag | 4924 | 8409 |
| Imm OT (3mg) 0.1 ug ag | 7235 | 24250 |
| Imm OT (3mg) 1 ug | 14605 | 70078 |
| Imm OT (3mg) 5 ag | 11995 | 74585 |
| Imm OT (1mg) no ag | 3558 | 7079 |
| Imm OT (1mg) 0.1 ug ag | 4871 | 16339 |
| Imm OT (1mg) 1 ug | 4949 | 39954 |
| Imm OT (1mg) 5 ag | 4172 | 37059 |
| Imm OT (0.1mg) no ag | 5661 | 5904 |
| Imm OT (0.1mg) 0.1 ug ag | 12094 | 8168 |
| Imm OT (0.1mg) 1 ug | 23445 | 12242 |
| Imm OT (0.1mg) 5 ag | 36710 | 11754 |

SEQUENCE LISTING

<160> NUMBER OF SEQ ID NOS: 3

<210> SEQ ID NO 1
<211> LENGTH: 669
<212> TYPE: DNA
<213> ORGANISM: Homo sapiens

<400> SEQUENCE: 1

```
taggcataaa ttggtctgcg caccagcacc atgcaacttt ttcacctctg cctaatcatc      60
tcttgttcat gtcctactgt tcaagcctcc aagctgtgcc ttgggtggct ttggggcatg     120
gacatcgacc cttataaaga atttggagct actgtggagt tactctcgtt tttgccttct     180
gacttctttc cttcagtacg agatcttcta gataccgcct cagctctgta tcgggaagcc     240
ttagagtctc ctgagcattg ttcacctcac catactgcac tcaggcaagc aattctttgc     300
tgggggggaac taatgactct agctacctgg gtgggtgtta atttggaaga tccagcgtct     360
agagacctag tagtcagtta tgtcaacact aatatgggcc taaagttcag gcaactcttg     420
tggtttcaca tttcttgtct cacttttgga agagaaacag ttatagagta tttggtgtct     480
ttcggagtgt ggattcgcac tcctccagct tatagaccac caaatgcccc tatcctatca     540
acacttccgg agactactgt tgttagacga cgaggcaggt cccctagaag aagaactccc     600
tcgcctcgca gacgaaggtc tcaatcgccg cgtcgcagaa gatctcaatc tcgggaatct     660
caatgttag                                                             669
```

<210> SEQ ID NO 2
<211> LENGTH: 219
<212> TYPE: PRT
<213> ORGANISM: Homo sapiens

<400> SEQUENCE: 2

```
Ile Gly Leu Arg Thr Ser Thr Met Gln Leu Phe His Leu Cys Leu Ile
1               5                   10                  15

Ile Ser Cys Ser Cys Pro Thr Val Gln Ala Ser Lys Leu Cys Leu Gly
            20                  25                  30

Trp Leu Trp Gly Met Asp Ile Asp Pro Tyr Lys Glu Phe Gly Ala Thr
        35                  40                  45

Val Glu Leu Leu Ser Phe Leu Pro Ser Asp Phe Phe Pro Ser Val Arg
    50                  55                  60

Asp Leu Leu Asp Thr Ala Ser Ala Leu Tyr Arg Glu Ala Leu Glu Ser
65                  70                  75                  80

Pro Glu His Cys Ser Pro His His Thr Ala Leu Arg Gln Ala Ile Leu
                85                  90                  95

Cys Trp Gly Glu Leu Met Thr Leu Ala Thr Trp Val Gly Val Asn Leu
            100                 105                 110

Glu Asp Pro Ala Ser Arg Asp Leu Val Val Ser Tyr Val Asn Thr Asn
        115                 120                 125

Met Gly Leu Lys Phe Arg Gln Leu Leu Trp Phe His Ile Ser Cys Leu
    130                 135                 140

Thr Phe Gly Arg Glu Thr Val Ile Glu Tyr Leu Val Ser Phe Gly Val
145                 150                 155                 160

Trp Ile Arg Thr Pro Ala Tyr Arg Pro Pro Asn Ala Pro Ile Leu
                165                 170                 175

Ser Thr Leu Pro Glu Thr Thr Val Val Arg Arg Gly Arg Ser Pro
            180                 185                 190
```

```
                                             -continued

Arg Arg Arg Thr Pro Ser Pro Arg Arg Arg Ser Gln Ser Pro Arg
            195                 200                 205

Arg Arg Arg Ser Gln Ser Arg Glu Ser Gln Cys
    210                 215

<210> SEQ ID NO 3
<211> LENGTH: 168
<212> TYPE: PRT
<213> ORGANISM: Artificial
<220> FEATURE:
<223> OTHER INFORMATION: HBcAG

<400> SEQUENCE: 3

Met Gln Ala Ser Lys Leu Cys Leu Gly Trp Leu Trp Gly Met Asp Ile
1               5                   10                  15

Asp Pro Tyr Lys Glu Phe Gly Ala Thr Val Glu Leu Leu Ser Phe Leu
            20                  25                  30

Pro Ser Asp Phe Phe Pro Ser Val Arg Asp Leu Leu Asp Thr Ala Ser
        35                  40                  45

Ala Leu Tyr Arg Glu Ala Leu Glu Ser Pro Glu Cys His Ser Pro His
    50                  55                  60

His Thr Ala Leu Arg Gln Ala Ile Leu Cys Trp Gly Glu Leu Met Thr
65                  70                  75                  80

Leu Ala Thr Trp Val Gly Val Asn Leu Glu Asp Pro Ala Ser Arg Asp
                85                  90                  95

Leu Val Val Ser Tyr Val Asn Thr Asn Met Gly Leu Lys Phe Arg Gln
                100                 105                 110

Leu Leu Trp Phe His Ile Ser Cys Leu Thr Phe Gly Arg Glu Thr Val
            115                 120                 125

Ile Glu Tyr Leu Val Ser Phe Gly Val Trp Ile Arg Thr Pro Pro Ala
        130                 135                 140

Tyr Arg Pro Pro Asn Ala Pro Ile Leu Ser Thr Leu Pro Glu Thr Thr
145                 150                 155                 160

Leu Glu His His His His His His
                165
```

TRANSMUCOSAL ADMINISTRATION OF AGGREGATED ANTIGENS

CROSS-REFERENCE TO RELATED APPLICATIONS

This application is a U.S. national phase application of PCT International Application No. PCT/US03/33178, filed on Oct. 17, 2003, which claims the benefit of U.S. Provisional Application No. 60/419,279, filed Oct. 17, 2002, the disclosures of each of which are herein incorporated by reference in their entireties.

BACKGROUND OF THE INVENTION

Numerous bacterial, viral, and parasitic infections of mammals have two phases of infection: an acute phase during the early stages of the infection, sometimes followed by a prolonged chronic phase having a finite or indefinite duration. The ability of an infectious agent to establish a chronic infection in a mammalian host depends to a significant extent on the capacity of the host immune response to eliminate the infecting organism from the host in the early stages of the infection. The specific immune mechanisms responsible for eliminating the infectious agent from the host differ depending on the infectious agent. In the case of viral and some parasitic infections, the infectious agent-eliminating activity of cytotoxic T lymphocytes is believed to comprise a pivotal component of the host immune response for mediating the elimination of these agents from the host.

The components of a mammalian immune system to which mammalian immune response activities can be attributed include, but are not limited to, antibody molecules, complement molecules, B lymphocytes, T lymphocytes, cytotoxic T lymphocytes, helper T cells, suppressor T cells, immunosuppressive lymphocytes, cytokine-secreting lymphocytes, other non-cytotoxic lymphocytes, macrophages, neutrophils, mast cells, basophils, eosinophils, monocytes, and the like. Induction or replication of the host immune activities leading to complete elimination of an infectious agent from a mammalian host is the paradigm for a clinical treatment for infection by a infectious agent.

In the course of infections with bacteria and some parasites, elimination from a host of an infectious agent causing an acute infection has traditionally been accomplished using antibiotics which serve as relatively selective poisons for the infectious agent. Antibiotic treatment has been less successful in the case of chronic bacterial infection. More recently, clinical efforts have focused on modulating the host immune system in an attempt to eliminate infectious agents causing chronic infections in cases wherein indolence of the host immune system contributes to persistence of the infectious agent. Specific immune modulation using substances such as interferons alpha, beta, and gamma has been attempted, and in a minority of cases beneficial results have been observed.

When an infection becomes chronic, the infection may be controlled by a persistent host immune reaction to the infectious agent. Certain herpes viruses, for example, remain latent only in the context of host immune competence. Immunosuppressive therapy used, for example, in organ transplant recipients permits latent herpes virus to become reactivated. Thus, loss of immune competence in response to steroid and cyclosporin A administration to a human patient having a latent HHV-6 infection permits recrudescence of HHV-6. The result of HHV-6 reactivation includes viral pneumonia and bone marrow suppression. In addition, the high incidence of non-Hodgkins B cell lymphomas among humans infected with the AIDS virus (HIV-1) demonstrates that pathogenicity attributable to chronic Epstein-Barr virus infections becomes active as T cell competence is lost. Thus, reactivation of pathogenicity attributable to an otherwise non-pathogenic chronic infection which is effected by suppression of the host's immune competence may have deleterious effects on the host.

The mucosal immune system includes those immune cells and organs directly associated with the mucosal lining of the gastrointestinal tract and lungs, including the airways. Such a partitioning of the body's total immune network is not arbitrary, but is based on certain widely recognized unique features of the mucosal immune system. One of the distinguishing features separating mucosal immunity from other types of immunity is the requirement that the mucosa physically transports, or permits ingress of foreign substances into the body. In the gut, nutritional substances must be absorbed for metabolic purposes. Many, and probably most of the absorbed nutrients are antigenic. Proteins, lipoproteins, carbohydrates complexed with proteins, and the like can and do stimulate immune priming and subsequent recognition. Further, because of the large concentration of symbiotic (but potentially pathogenic) microorganisms in the gastrointestinal tract, the mucosal immune system must prevent adverse immune reactions that would result in elimination of the symbionts through inflammatory immune recognition.

Another distinctive feature of the mucosal immune system is the ability to generate a specific isotype of antibody (IgA) which can prevent absorption of antigen but is non-inflammatory. While certain sub-classes of IgG are similarly non-inflammatory, IgA is predominantly localized to the mucosal immune system.

It is also recognized by those skilled in the art, that the mucosal immune system is the numerically dominant member of somatic immunity. Studies have shown that each meter of human intestine contains approximately $10^{12}$ lymphocytes. On the basis of immunoglobulin-secreting cells, the human gut contains several-fold more cells than the remainder of the immune system. Additionally, the phenotypic character of the immunocytes populating the mucosal immune system is distinctive. Murine and human intestine contain a large percentage (up to 90%) of an atypical lymphocyte; the gamma-delta T lymphocyte. These cells are unique because they are not educated in the thymus during ontogeny as are the majority of alpha-beta T cells populating the spleen, peripheral lymph nodes, or circulation.

Yet another feature of the mucosal immune system that separates it from the somatic immunoaxis is the presence of predominantly anti-inflammatory T helper 2 cytokines. The tissue supporting the single-cell barrier separating the lumen of the gastric or respiratory system from the external milieu, the lamina propria, is rich in interleukin-4, interleukin-10, and transforming growth factor-b. It is known to those skilled in the art that immune cells antigenically stimulated in such an environment differentiate into immune effectors with anti-inflammatory (TH2) functions. However, such an environment does not guarantee ultimate TH2 function, and this has been shown to occur in the mucosal immune system. Specifically, antigen presentation to the mucosal immune system typically has three outcomes as set forth below.

1. When an antigen is transported across the mucosal epithelium, it can be processed by immune accessory cells, which may migrate to local immune accessory organs (regional lymph nodes) and there cognitively present antigen or antigen fragments to other immune cells resulting in the numerical expansion of antigen-reactive lymphocytes. A proportion of the activated lymphocytes mature to plasma cells that manufacture the mucosal-dominant, non-inflammatory immunoglobulin IgA. Another proportion of the cells differentiates into inflammatory (TH1) cells such as IgG2a secreting plasma cells, interferon-gamma or Interleukin-2 expressing T helper lymphocytes.

2. Some of the processed antigen is presented to immature B lymphocytes that differentiate into IgA secreting plasma cells. These cells migrate back to the mucosa where they establish residence, and express the specific immunoglobulin. The majority of the immune protein is then transported into the lumen of the gut or lungs where it reacts with epitopes of the educating antigen. Resultant antibody binding to the immunogen can prevent transmucosal ingress.

3. The mucosal immune system, perhaps due to its unique physiological responsibilities, concomitantly drives one of two additional immunological events. These events are not mutually exclusive, and are believed to occur in a continuum dictated by the amount of antigen administered as well as dose timing, frequency, and simultaneously administered proteins. The first of these events is the education and expansion of another arm of the immune system (low dose tolerance).

When small (ca. unit milligram) amounts of the antigen are presented to the mucosa, a set of lymphocytes is enabled for education and expansion. The distinguishing characteristic of this subset of educated cells is their ability to accept a biochemical signal of active inflammation and recognize the presence of the original educating antigen in intimate physical proximity to sites of inflammation. When both activation criteria are present, the suppressor lymphocytes express certain immune regulatory cytokines resulting in an active down regulation of the inflammatory reaction. These biochemicals include interleukin-4, interleukin-10 and TGF-B.

A second mechanism of tolerance engendered by antigen presentation to the mucosal immune system is referred to as "high-dose tolerance". This mechanism comes into play following administration of larger (ca. 10 mg or larger) amounts of the educating antigen. "High dose" tolerance appears to directly disable the antigen-reactive lymphocyte. It has been suggested that the administration of large amounts of antigen results in a reduced proteolytic processing of the antigen in the gut or lungs with an increased concomitant availability of non-degraded antigen which is transferred across the mucosal barrier intact. Reactive lymphocytes bind large amounts of the antigen, and are rendered anergic perhaps because the stoichiometry of antigen presentation with required activation signal, although other explanations have been offered. Experimentally, the two mechanisms are differentiated by the demonstrable requirement for educating antigen and presence of IL-4, IL-10, and TGF-B in immunosuppressed cultures or animal models in the first instance. In contrast, anergy is experimentally demonstrated by reversal of immune unresponsiveness by the addition of exogenous IL-2, and the relative paucity of suppressive cytokines present in active suppression.

Published work from several laboratories has confirmed that both of the above-described mechanisms may operate concomitantly. The foregoing discussion is provided to clarify the known mechanisms of oral tolerance, and not to differentiate them. Both operate to suppress immune responsiveness to mucosally presented antigen, and appear to be functional in the suppression of inflammatory responses to inhaled or eaten foreign substances.

Virtually all mucosally presented antigens elicit tolerance. Low dose tolerance occurs following the administration of myelin basic protein in a model of multiple sclerosis, type II collagen in a model of rheumatoid arthritis, retinal S antigen in a model of autoimmune uvitis and insulin in a model of type I diabetes. Further, mice fed recombinant acetylcholine end plate receptor protein have been found to be refractory to immune stimulation with the same protein in a model of myasthenia gravis. Additionally, oral ovalbumin administration has been shown to elicit tolerance in ovalbumin-TCR transgenic mice. High dose tolerance has also been reported for some of the same as well as different proteins.

There are certain reported exceptions in the otherwise universal ability of orally or nasally administered proteins to establish oral tolerance. These exceptions may be divided into two categories based on either the biochemical properties of the administered protein or the physical form of the antigen. The oral administration of cholera holotoxin resulted in systemic immunity based on several experimental criteria. Similarly, the mucosal exposure of mice to the heat labile enterotoxin of certain $E.\ coli$ strains resulted in the presence of circulating IgG antibodies reactive with the protein. Both of these substances belong to a unique class of toxins that are known to activate phosphorylation of specific transmembrane receptors present in enterocytes in the mucosa. Additionally, the diseases caused by the microorganisms that produce these proteins are enteric, and thus, the proteins are known to be naturally pathogenic at the mucosal level.

The second form of exception to orally administered proteins inducing an immune response instead of tolerance concerns the physical form of the presented antigen. Arntzen and colleagues reported the presence of systemic antibodies reactive with the nucleocapsid of Norwalk virus after feeding extracts of tobacco containing the transgenically expressed virus product (Arntzen et al., 1996, PNAS 93(11):5335-40). These researchers also discovered the presence of systemic immunity to hepatitis B surface protein (HBsAg) in mice fed repeated doses of following isolation of the protein expressed in a similar transgenic plant system (Kong et al., 2001, PNAS 98(20):11539-44.). However, the simultaneous administration of the mucosal adjuvant cholera holotoxin was required for maximal effect. A minor response was induced by feeding primed mice the plant extract alone, perhaps due to the physical form of the antigen. Importantly, apparently intact 17 nM pseudovirions were seen in homogenates of the plants, indicating that the transgenic protein self-assembled within the plant tissues Another example of the ability of orally presented antigens to elicit an immune response is found in the recent work of Koprowski and colleagues. These investigators inserted the coding sequences for two protective epitopes from the rabies virus into alfalfa mosaic virus coat protein (CP), and then rescued the transgenic protein by enabling viral replication in plants in a complemented system using either tobacco mosaic virus lacking native CP(A4-g24), or in trans following infection with infectious alfalfa mosaic virus. Mice fed the chimeric viral particles were found to develop a systemic immune responsiveness (Yusibov et al., 2002, Vaccine 20(25-26):3155). Kapusta et. al. engineered a commercial cultivar of tomato to express the coat protein of the rabies virus, and reported that mice fed freeze-dried fruit became immune to challenge with normally lethal concentrations of the virus (Kapusta et al., 2001, Adv. Exp. Med. Biol. 495:299-303). Additional work by these researchers provided evidence that tomato's expressing the HBsAg could elicit circulating antibodies in mice formally adequate to provide immune protection from infection based on established IgG concentrations in humans (Kapusta et al., 1999, FASEB J. 13(13):1796-9). These results, collectively, suggest that oral administration of certain vaccine antigens results in the boosting of immunologically primed animals, or in rare cases the establishment of protective immunity in immunologically naive mice, but not the anticipated immune indolence of mucosal tolerance. An important common feature of these results is that the transgenically expressed antigen was either biochemically constrained to assemble into macromolecular structures, or was detected as complexed with plant organelles such as Golgi bodies, vesicles, plasma lemma and cell walls; structures effectively forming macromolecular complexes.

There is a long felt need in the art for efficient methods of immunizing a patient against an antigen. There is also a need for a method of presenting antigens to efficiently induce mucosal tolerance. The present invention meets these needs.

SUMMARY OF THE INVENTION

The present invention includes a method of inducing a systemic immune response to a peptide in a mammal, wherein one of the method steps involves transmucosally administering to the mammal a macromolecular aggregate of the peptide, thereby inducing a systemic immune response in the mammal.

In an aspect of the invention, a method of inducing an immune response includes administration of a macromolecular aggregate of at least 10 peptide subunits, and more preferably, at least 20 subunits. In another aspect of the invention, the macromolecular aggregate may have a molecular weight in excess of 1,000 kD.

In one aspect of the present invention, a method of inducing an immune response includes administration of a macromolecular aggregate of at least 1 nm in diameter, and more preferably, at least 5 nm in diameter.

In an embodiment of the present invention, a method of inducing a systemic immune response involves administering a macromolecular aggregate resistant to digestive degradation. In one aspect of the invention, a macromolecular aggregate is resistant to digestive degradation through stabilization in aggregate form by chemical treatment. In another aspect of the invention, the macromolecular aggregate is stabilized in aggregate form by recombinant protein engineering of the peptide. In yet another aspect of the invention, the macromolecular aggregate of a peptide stabilized in aggregate form by recombinant protein engineering is further stabilized in aggregate form by subsequent chemical treatment.

In an embodiment of the present invention, a method of inducing an immune response includes administration of a macromolecular aggregate of a protein derived from hepatitis B. In one aspect of the invention, the macromolecular aggregate is an aggregate of hepatitis B viral surface protein. In another aspect of the invention, the macromolecular aggregate is an aggregate of hepatitis B viral nucleocapsid protein. In yet another aspect of the invention, the macromolecular aggregate is an aggregate of hepatitis B viral envelope protein.

An embodiment of the present invention provides a pharmaceutical composition for inducing systemic immunity in a mammal, wherein the pharmaceutical composition includes a macromolecular aggregate of a peptide and a suitable pharmaceutical carrier, in an amount sufficient to induce systemic immunity when administered to a mammal transmucosally.

In another embodiment of the invention, a method of suppressing a systemic immune response to a peptide in a mammal already immune to that peptide is provided. Such a method of suppressing a systemic immune response in a mammal includes transmucosal administration of a macromolecular aggregate of the peptide to a mammal in order to suppress a systemic immune response.

In an aspect of the invention, a method of suppressing an immune response includes administration of a macromolecular aggregate of a peptide composed of less than 20 subunits of the peptide. In another aspect of the invention, the method of suppressing an immune response includes administration of a macromolecular aggregate of at less than 1 nm in diameter.

In an embodiment of the present invention, a method of suppressing a systemic immune response involves administering a macromolecular aggregate resistant to digestive degradation. In one aspect of the invention, a macromolecular aggregate capable of suppressing a systemic immune response is resistant to digestive degradation through stabilization in aggregate form by chemical treatment. In another aspect of the invention, the macromolecular aggregate is stabilized in aggregate form by recombinant protein engineering of the peptide. In yet another aspect of the invention, the macromolecular aggregate of a peptide stabilized in aggregate form by recombinant protein engineering is further stabilized in aggregate form by subsequent chemical treatment.

In an embodiment of the present invention, a method of suppressing an immune response includes administration of a macromolecular aggregate of a protein derived from hepatitis B. In one aspect of the invention, the macromolecular aggregate is an aggregate of hepatitis B viral surface protein. In another aspect of the invention, the macromolecular aggregate is an aggregate of hepatitis B viral nucleocapsid protein. In yet another aspect of the invention, the macromolecular aggregate is an aggregate of hepatitis B viral envelope protein.

An embodiment of the present invention provides a pharmaceutical composition for suppressing systemic immunity in a mammal, wherein the pharmaceutical composition includes a macromolecular aggregate of a peptide and a suitable pharmaceutical carrier, in an amount sufficient to induce systemic immunity when administered to a mammal transmucosally.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is the DNA sequence of the HBcAg gene (SEQ ID NO:1) and the amino acid sequence for the corresponding protein (SEQ ID NO:2) for HBcAg from HBV serotype ayw. The sequence was obtained from the National Library of Medicine.

FIG. 3 is a graph illustrating that Con A stimulated spleen cells from normal mice proliferated equally in the presence or absence of native HBsAg at various concentrations. Briefly, spleen cells from a normal mouse were collected and placed in culture. Con A (5 µg/well) was added and serial dilutions of native HBsAg was added. The concentrations ranged from 0 µg/well to 20 µg/well in 2-fold dilutions. Proliferation was determined as described.

FIG. 4 is a graph illustrating that oral administration of native HBsAg boosts the immune response of antigen-challenged spleen cells from immune mice. Briefly, mice were immunized with the native antigen, boosted, and some of the mice were then orally tolerized with native HBsAg (pseudovirions) at the concentrations indicated. Following treatment, the mice were euthanized, and then the spleen cell suspensions were prepared and challenged with the appropriate antigen. Proliferation of the cells was quantified by $^3$H-Tdr incorporation and scintillography.

DETAILED DESCRIPTION OF THE INVENTION

Figure 2:
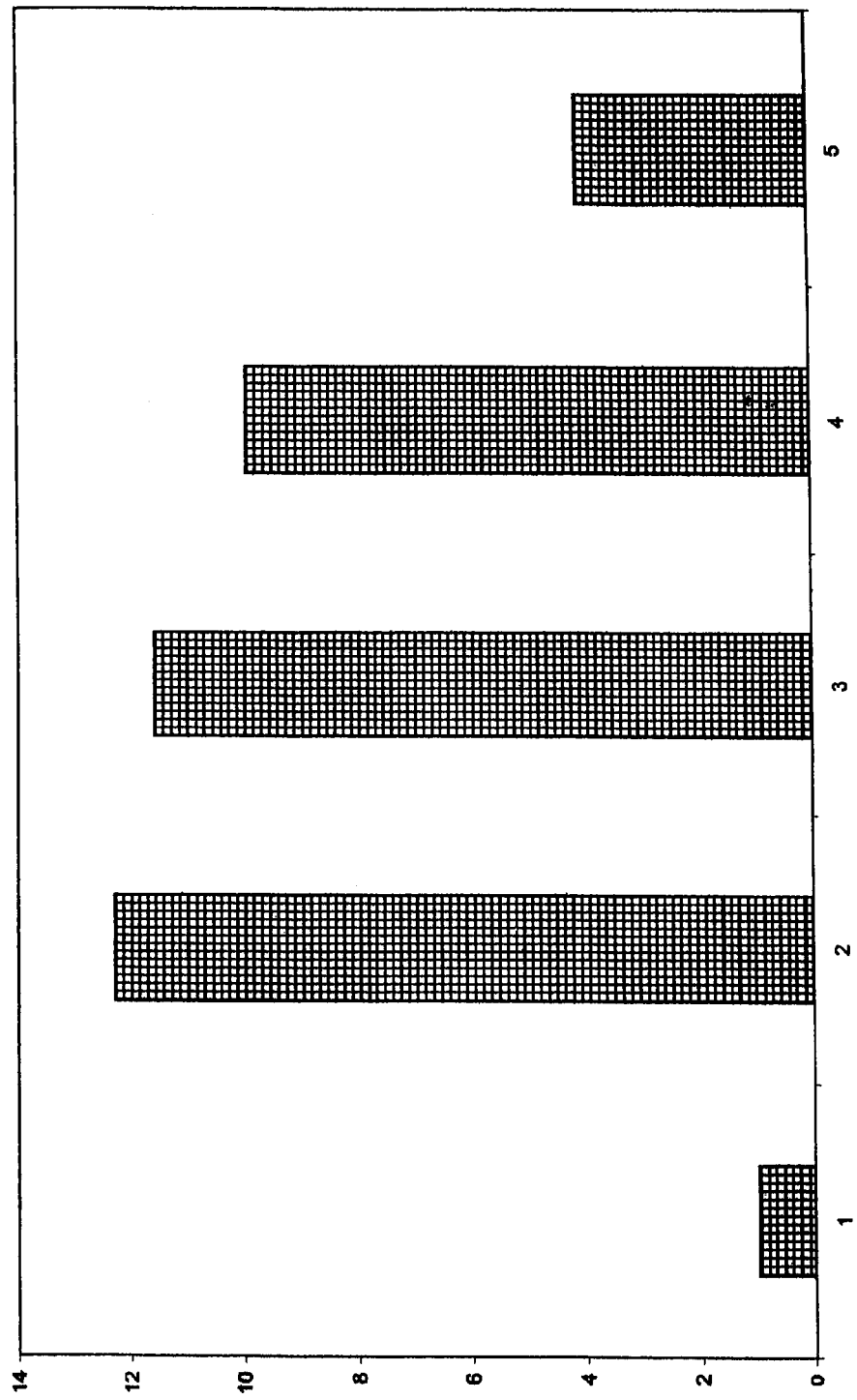
FIG. 2 is a graph illustrating that the oral administration of ag HBcAg to previously immunized mice induces suppression of the proliferation of antigen challenged immune splenocytes in culture. Column 1 indicates whether the mice were immunized, boosted and orally tolerized as described. Column 2 depicts the response of spleen cells from mice sham tolerized with PBS and antigen challenged. Columns 3 through 5 represent the proliferation of spleen cells from animals tolerized with 0.0, 0.1, 1 and 10 of ag HBcAg, respectively.

Foreign substances presented to the mucosa of the gastrointestinal tract or the lungs act as immunogens. Because these mucosal surfaces are unit cellular thickness and have the physiological responsibility of absorption, foreign substances are known to elicit immune stimulation. To prevent adverse immune reactions in the host, a physiological compensatory mechanism has evolved. This mechanism is alternatively called oral or mucosal tolerance. Two forms of mucosal tolerance are known to those skilled in the art. In the case of "low dose" tolerance, antigens eliciting an immune response concomitantly elicit educated lymphocytes capable of suppressing inflammatory immune reactions upon experiencing specific stimuli consisting of A) at least one biochemical signal of inflammation and B) the educating antigen in intimate physical proximity. The second, mechanism, "high dose" tolerance results in anergizing inflammatory cells. The two mechanisms are not mutually exclusive, and may both operate in an individual at the same time. Both forms of tolerance are useful for treating certain diseases in animals, including humans.

In one preferred embodiment, a class of diseases, termed autoimmune diseases, may be attenuated or suppressed by the oral or by inhalation administration of antigens known to be among the immune targets attacked by an individual's immune system. This therapeutic application is described by the teachings of Weiner and associates in U.S. Pat. Nos. 6,077,509, 6,039,947, 6,036,957, 6,019,971, 5,961,977, 5,935,577, 5,869,093, 5,869,054, 5,858,980, 5,858,968, 5,858,364, 5,856,446, 5,849,298, 5,843,886, 5,843,445, 5,840,848, 5,807,993, 5,783,188, 5,788,968, 5,783,188, 5,763,396, 5,733,547, 5,720,955, 5,681,556, 5,643,868, 5,641,474, 5,641,473, 5,593,698, 5,571,500, and 5,571,499.

In yet another preferred embodiment of the therapeutic approach, the disease following certain chronic infections of animals may be attenuated or suppressed by mucosal tolerance therapy as taught in U.S. Pat. No. 6,355,248, incorporated by reference herein in its entirety, wherein the disclosed invention uses physiochemical forms and compositions of the tolerogens used to engender mucosal tolerance for the latter preferred embodiment.

The dichotomy of oral tolerance induced by most fed or inhaled antigens versus the induction of systemic immunity following the oral presentation of other antigens is resolved by the present invention. Specifically, the present invention teaches that the physical form of the peptide administered dictates which natural course ensues following mucosal administration of the antigen. More specifically, the present invention teaches that peptides that are biochemically constrained to assemble into macromolecular aggregates of greater than approximately 10, but preferably about 20 subunits, or which approach physical sizes greater than 1 nm, but preferably greater than 5 nm in the largest diameter engender selective uptake by M cells of the Peyer's patches of the intestine resulting in systemic immunity. Antigens that are expressed as monomolecular species or those that are engineered or physically/chemically treated to prevent macromolecular assembly engender oral tolerance instead. This is important because the generation of immunity following oral presentation of antigen may exacerbate disease in patients with chronic infections and treated with mucosal tolerance induction as taught in U.S. Pat. No. 6,355,407.

Additionally, the present invention teaches that assemblies of monomer subunits that are resistant to digestive degradation also enhance the development of systemic immunity as opposed to mucosal tolerance. The present invention is also useful in that the formulation of the composition of antigen may be specifically directed to induce oral tolerance. The invention is also useful for the design and composition of therapeutic agents for the treatment of a subset of chronic infections described in U.S. Pat. No. 6,355,407.

The present invention also provides an improved method of treating a chronic infection of a mammal by an infectious agent, the improved method comprising any known method of treating the chronic infection performed in conjunction with administration on to the mammal of a composition comprising an epitope located in close proximity to a site of undesirable chronic immune reactivity. This is important because such combination methods of the present invention will allow a finer control of the induction of either oral tolerance or systemic immunity as described elsewhere herein, while providing targeted drug therapy at the same time.

A known method of drug treatment of a patient according to the present invention may be performed before, after, or simultaneously with administration of the epitope. For example, the known method may be performed within one month of administration of the epitope, and is preferably performed within one week of administration of the epitope. Such known methods include administration of such compounds as lamivudine, a bacterial lipopolysaccharide, an immunoregulatory lipoprotein, a peptide covalently linked to tripalmitoyl-5-glycarylcysteinyl-seryl-serine, a steroid, cyclosporin A, azidothymidine (AZT), dideoxycytidine (ddC), dideoxyinosine (ddI), lamivudine (3TC), and the like.

DEFINITIONS

The articles "a" and "an" are used herein to refer to one or to more than one (i.e. to at least one) of the grammatical object of the article. By way of example, "an element" means one element or more than one element.

A "peptide" as the term is used herein is an oligopeptide, polypeptide, peptide, protein, glycoprotein, or lipoprotein. For example, the use of the term "peptide" herein includes a peptide having a sugar molecule attached thereto when a sugar molecule is attached thereto. A "peptide" as the term is used herein also includes a homogeneous multi-molecular peptide complex (i.e., a complex comprised of identical "peptide" subunits), a heterogeneous multi-molecular peptide complex (i.e., a complex comprised of more than one particular "peptide" subunit), and a monomolecular peptide.

A "macromolecular peptide aggregate" is defined herein as an associated collection of two or more peptides. The peptide molecules of a macromolecular peptide aggregate are associated by covalent or ionic interactions, by lipophilic interactions, by a mixture of both covalent and ionic interactions, or by a mixture of any of the above. A macromolecular peptide aggregate of the invention may be homogeneously comprised of identical peptide subunits, or may be comprised of a heterogeneous mixture of subunits. By way of a non-limiting example, a macromolecular peptide aggregate of the invention may be comprised of a mixture of wild type and mutant subunits of "peptide X."

A macromolecular peptide aggregate as used herein describes a physical association of two or more units of individual peptide molecules. The peptide molecule may associate specifically or non-specifically. By way of a non-limiting example, the "non-specific macromolecular aggregation" of a peptide according to the present invention may involve an ionic- and/or hydrophobic-based interaction of peptides effected by either increasing or decreasing the salt concentration of a peptide solution. By way of another non-limiting example, a "specific macromolecular aggregation" of the present invention may involve a rationally-designed amino acid mutation (or multiple amino acid mutations) that allows the mutated peptide to specifically associate with other, similar mutated peptides in a controlled manner. Specific association by way of the latter example may also be effected, enhanced, or decreased with the assistance of chemical compounds known by one of skill in the art to be useful in modulating peptide and peptide interactions.

A "non-peptide macromolecular aggregate" as the term is used herein refers to any macromolecular aggregate that consists of non-peptide chemical and biochemical moieties. A macromolecular aggregate is a physical association of two or more units of individual molecules. The molecules comprising an aggregate may associate specifically or non-specifically. The molecules comprising an aggregate may associate through ionic, non-ionic, or covalent interactions. Molecules useful in non-peptide macromolecular aggregates of the invention include, but are not limited to carbohydrates, including polysaccharides, oligosaccharides, and monosaccharides, lipids, and chemical moieties.

A "mixed species macromolecular aggregate" as the term is used herein refers to a macromolecular aggregate comprised of at least one peptide moiety and at least one non-peptide moiety.

The "mucosal immune system" is defined herein as those immune cells and organs directly associated with the mucosal lining of the gastrointestinal tract and lungs, including the airways. Such a partitioning of the body's total immune network is not arbitrary, but is based on certain widely recognized unique features of the mucosal immune system.

The term "recombinant peptide engineering" is used herein to denote a genetic or molecular biology-based method of altering the nucleic acid sequence encoding the naturally-occurring amino acid sequence of a peptide. Such a method may employ one or more of a random, iterative, calculated, rational design, or molecular modeling-based technique in order to mutate, add, or subtract amino acid residues from the naturally-occurring amino acid sequence of a peptide for the purpose of altering the native properties of the naturally-occurring peptide. Such properties include, but are not limited to, thermal stability, pH stability, stability as a function of ionic strength, primary-, secondary-, tertiary-, or quaternary structure, oligomeric state, and interaction with accessory peptides or cofactors.

As used herein, "modulating an immune response of a mammal" means increasing or decreasing either the amount of a component of the immune system or the activity by which a component of the immune system is characterized. By way of example, modulating an immune response of a human includes increasing the number of suppressor T lymphocytes present in the human, increasing secretion of immunosuppressive factors by a suppressor T lymphocyte in the human, decreasing the number of cytotoxic T lymphocytes present in the human, decreasing the cytotoxic activity of a cytotoxic T lymphocyte in the human, decreasing the amount of an antibody in the human, decreasing the amount of a complement protein in the human, decreasing the ability of a complement protein to interact with a cell in the human, and the like.

As used herein, an "antigen" refers to a substance that, as a result of coming in contact with appropriate cells, induces a state of sensitivity and/or immune responsiveness and that reacts in a demonstrable way with antibodies and/or immune cells of the sensitized subject in vivo or in vitro.

As used herein, an "epitope" means a molecule or a portion of a molecule which interacts or is capable of interacting with an immunoglobulin molecule produced by the immune system of a mammal such as a human. An antigen is a well known example of an epitope, or an epitope-containing molecule, that is capable of interacting with an antibody. It is understood that a single molecule may comprise numerous epitopes, and that an epitope may comprise a portion of each of more than one molecule. As used herein, an epitope may be a single molecule, a monomolecular species, a homogeneous macromolecular peptide aggregate, or a heterogeneous macromolecular peptide aggregate.

An "epitope located in close proximity to the immune response" means an epitope present on the surface of at least one cell of a tissue located at a site of undesirable immune reactivity, wherein the reactivity is induced or exacerbated by the presence in the mammal of the infectious agent, or an epitope which is cross-reactive with such an epitope. By way of example, the presence of the hepatitis B virus (HBV) induces the human body to produce cytotoxic T lymphocytes which attack hepatic cells that display a viral protein comprising a particular epitope on their surface. In this case, both production of these T lymphocytes and the cytotoxic activity of these T lymphocytes toward hepatic cells are undesirable immune reactivities. By transmucosally administering to an HBV-infected human a composition comprising the same or a similar epitope, immunosuppressive lymphocytes such as suppressor T lymphocytes are produced by the body. These lymphocytes are capable of migrating to the hepatic tissue which displays the epitope and of suppressing the cytotoxic activity of T lymphocytes produced in response to the presence in the human of HBV, thereby modulating the undesirable immune reactivity.

A first epitope is "cross-reactive" with a second epitope if the first epitope interacts or is capable of interacting with an immunoglobulin molecule produced by the immune system of a mammal such as a human and the second epitope interacts or is capable of interacting with the same immunoglobulin molecule.

The immune response modulated by the method may be an autoimmune reaction, a humoral immune response to infection by the infectious agent, a humoral immune response to infection by the infectious agent wherein the humoral response comprises production of an antibody which cross-reacts with a tissue antigen of the mammal, a cellular immune response to infection by the infectious agent, a cellular immune response to infection by the infectious agent wherein the cellular response comprises production of a cytotoxic cell which specifically induces cell death in a tissue of the mammal, and the like.

Humoral immune responses which can be modulated using the method of the invention include, but are not limited to, production of an antibody molecule by the mammal, production of a cytokine by the mammal, production of a complement protein molecule by the mammal, and the like. Cellular immune responses which can be modulated using the method of the invention include, but are not limited to, production of an antibody-producing cell, production of a cytotoxic T lymphocyte, production of a suppressor T cell, production of a T helper cell, production of an immune memory cell, and the like.

As used herein, the term "systemic immune response" refers to an immune response that is not solely a mucosal immune response in a mammal. A systemic immune response may be either cell-mediated or humoral. "Inducing a systemic immune response" refers to the act of bringing about an immune response in a mammal, wherein the immune response is not solely a mucosal immune response. A "mucosal" immune response is an immune response that occurs in a mucosal tissue of a mammal.

The term "antigenic tolerance" as used herein refers to the induction of immune hyporesponsiveness following transmucosal administration of an epitope, and should not be confused with the use of the term "systemic tolerance" which refers to a circulatory immune system phenomenon. "Systemic tolerance" may be differentiated from antigenic tolerance in that the former term is applied to the functional silencing, or deletion of clones of immune cells which develop in the thymus of a mammal and which recognize normal host tissue antigens. "Antigenic tolerance" specifically refers to the induction of hyporesponsiveness to a specific epitope following the transmucosal delivery of the epitope.

A first epitope is "located in close proximity to a second epitope" in a mammal if the first epitope and the second epitope are displayed by the same tissue, the first epitope is displayed by a first tissue which contacts a second tissue which displays the second epitope, or the first epitope is displayed by a first tissue in fluid communication with a second tissue which displays the second epitope. The ability to modulate an immune response elicited in response to the presence in a mammal of a first epitope by administering to the mammal a composition comprising a second epitope, wherein the first and second epitopes are located in close proximity to one another is designated "bystander suppression."

"Bystander suppression," as the term is used herein, is the result of the ability of transmucosally induced tolerant immune cells to migrate to sites of active inflammation and modulate immune reactions by secreting immunosuppressive factors such as transforming growth factor beta (TGF-.beta.) and interleukin-10 (IL-10). For example, mammals which have been immunized with the central nervous system protein, myelin basic protein (MBP), develop a disease which is similar to multiple sclerosis in humans. If a mammal is fed MBP, the disease state can be prevented, attenuated, or completely abrogated by induction of oral tolerance toward MBP. The same disease can be likewise prevented, attenuated, or completely abrogated if animals are fed phospholipid protein, a protein which is located in close proximity to MBP in the mammalian brain. Thus, it is not necessary to identify and administer to the host the specific host epitope(s) which is recognized by a component of the host immune system which is activated in response to the presence of an infectious agent. Instead, it is sufficient to administer to the host another epitope which is normally located in close proximity to the anatomical site of the autoimmune reaction.

A first epitope is "located in close proximity to an immune response" if the immune response is elicited in response to the presence in a mammal of the first epitope, the immune response is elicited in response to the presence in the mammal of a second epitope located in close proximity to the first epitope, or if the presence in the Mammal of a second epitope elicits an immune response which cross-reacts with the first epitope.

An epitope is "displayed by" a tissue, as used herein, when the epitope is associated with a cell of the tissue and is accessible to a component of the immune system of the mammal which comprises the tissue. By way of example, a cell-surface protein of an epithelial cell lining an artery of a mammal is accessible to an antibody in the bloodstream of the mammal. Thus, an epitope of such a cell-surface protein is displayed by mammalian arterial epithelial tissue. An epitope is displayed by a tissue of a mammal if the epitope is normally expressed by the tissue, or if the epitope is expressed by the tissue following infection of the mammal by an infectious agent.

"Transmucosal administration," as the term is used herein, refers to the administration of an antigen to a mammal by contacting the antigen with a mucosal surface of a mammal. A mucosal surface of a mammal is generally known to one of ordinary skill in the art. Mucosal surfaces useful in the present invention include, but are not limited to the mucosal surfaces of the oral cavity, the gastrointestinal system, the rectal cavity, the nasal cavity, and the nasopharyngeal cavity.

The term "chemical treatment" refers to the modification of a biological or chemical substance by contacting the biological or chemical substance with a chemical compound, thereby altering the chemical composition of the biological or chemical substance. For example, a peptide antigen may be contacted with a chemical crosslinking reagent, resulting in the covalent addition of a chemical crosslinker to the peptide antigen. By way of another example, a peptide antigen may be contacted with a chemical modifying agent, resulting in the covalent modification of an amino acid side chain of the peptide antigen, rendering the peptide antigen reactive with a second peptide antigen.

"Digestive degradation" of an antigen refers to the enzymatic or chemical dissolution of one or more chemical bonds in the antigen. For example, digestive degradation of a peptide antigen may include the action of a proteolytic enzyme on at least one peptide bond in a peptide antigen.

Methods of Modulating an Immune Response

The goals of eliminating and preventing infection in a mammal rely upon the immunity of a mammal. The present invention features methods of modulating an immune response in a mammal. In particular, the present invention features methods of inducing a systemic immune response to a peptide in a mammal, as well as methods of inducing oral tolerance to a peptide in a mammal. This is because it has now been discovered that the physical form of a peptide transmucosally introduced to a mammal plays a role in the determination of the type of immunity—either oral tolerance or systemic immunity—engendered in the mammal.

As described more fully herein below, the present invention discloses for the first time that, surprisingly, a transmucosally-introduced low dose of a macromolecular aggregate of a peptide can engender systemic immunity. Further, as described more fully herein below, the present invention also discloses for the first time that, surprisingly, a transmucosally-introduced low dose of a certain physical forms of a macromolecular aggregate of a peptide can engender oral tolerance. This is significant, because until the present invention, it was believed that only a high dose of a transmucosally-introduced peptide could produce systemic immunity, and that a low dose of a transmucosally-introduced peptide could only produce oral tolerance.

In an embodiment of the present invention, a macromolecular aggregate of a peptide is transmucosally administered to a mammal. Upon administration of a macromolecular aggregate of a peptide to a mammal, the peptide is taken up by the local mucosa with which it is in proximity. Transmucosal uptake of a peptide subsequently elicits an immune response. As known to one skilled in the art, and as described elsewhere herein, transmucosal uptake of a peptide results in a number of events, including processing of the peptide antigen by immune accessory cells, presentation of the processed antigen to immature B lymphocytes, and either a "low dose" or a "high dose" response, based upon the concentration of the peptide antigen taken up transmucosally.

A "low dose" response generally occurs when small (ca. unit milligram) amounts of the antigen are presented to the mucosa, and a set of lymphocytes is enabled for education and expansion. The distinguishing characteristic of this subset of educated cells is their ability to accept a biochemical signal of active inflammation and recognize the presence of the original educating antigen in intimate physical proximity to sites of inflammation. When both activation criteria are present, the suppressor lymphocytes express certain immune regulatory cytokines resulting in an active down regulation of the inflammatory reaction. A non-limiting example of such biochemicals includes interleukin-4, interleukin-10 and transforming growth factor beta (TGF-$\beta$).

A "high-dose" response, also known as "high-dose tolerance," comes into play following administration of larger (ca. 10 mg or larger) amounts of the educating antigen. "High dose" tolerance appears to directly disable the antigen-reactive lymphocyte. It has been suggested that the administration of large amounts of antigen results in a reduced proteolytic processing of the antigen in the gut or lungs with an increased concomitant availability of non-degraded antigen which is transferred across the mucosal barrier intact. Reactive lymphocytes bind large amounts of the antigen, and are rendered anergic.

Therefore, it is a feature of the present invention to provide methods for selectively obtaining an immunological response in a mammal. In an embodiment of the invention, a macromolecular peptide aggregate is transmucosally administered to a mammal. Upon administration of the peptide antigen, the peptide is taken up by the mucosa with which the peptide antigen is in proximity. In this embodiment, the uptake of the peptide antigen engenders a low-dose response in the mammal. Therefore, a method of the present invention includes transmucosal administration of a macromolecular peptide aggregate to a mammal to engender a low-dose immune response. In another aspect of the invention, a method of the invention includes transmucosal administration of a macromolecular peptide aggregate to a mammal to engender mucosal tolerance.

Low-Dose Immunity

In an aspect of the invention, the macromolecular peptide aggregate responsible for engendering a low-dose response is a complex comprising fewer than 21 subunits of the peptide. This is because it has been shown for the first time herein that macromolecular peptide aggregates containing fewer than 21 peptide subunits engender a low-dose immune response in a mammal resulting in mucosal tolerance. Therefore, a method of the present invention includes transmucosal administration of a macromolecular peptide aggregate of fewer than 21 peptide subunits to a mammal to engender a low-dose immune response. In another aspect of the invention, a method of the invention includes transmucosal administration of a macromolecular peptide aggregate of fewer than 21 subunits to a mammal to engender mucosal tolerance. In an embodiment of the invention, a macromolecular peptide aggregate contains about 20 subunits. In another embodiment, the macromolecular peptide aggregate contains between about 15 subunits and about 20 subunits. In another embodiment, the macromolecular peptide aggregate contains between about 10 subunits and about 15 subunits. In another embodiment, the macromolecular peptide aggregate contains between about 5 subunits and about 10 subunits. In another embodiment, the macromolecular peptide aggregate contains between about 1 subunit and about 5 subunits.

In yet another embodiment of the invention, a peptide administered to a mammal is administered as a monomolecular species. A monomolecular peptide of the invention is useful for the stimulation of a "low-dose" response in a mammal. In another aspect of the invention, a monomolecular peptide of the invention is useful for the stimulation of mucosal tolerance in a mammal. As discussed in greater detail elsewhere herein, one of skill in the art will know, when armed with the disclosure set forth herein, how to make and use a monomolecular peptide of the present invention.

In an aspect of the invention, a macromolecular peptide aggregate responsible for engendering a low-dose response is a multiple subunit complex of less than 5 nm in diameter. This is because it has been shown for the first time herein that macromolecular peptide aggregates of less than 5 nm in diameter engender a low-dose immune response resulting in mucosal tolerance. Therefore, a method of the present invention includes transmucosal administration of a macromolecular peptide aggregate of less than 5 nm in diameter to a mammal to engender a low-dose immune response. In another aspect of the invention, a method of the invention includes transmucosal administration of a macromolecular peptide aggregate of less than 5 nm in diameter to a mammal to engender mucosal tolerance. In an embodiment of the invention, a macromolecular peptide aggregate is about 5 nm in diameter. In another embodiment, the macromolecular peptide aggregate is between about 3 nm and about 5 nm. In another embodiment, the macromolecular peptide aggregate is between about 1 nm and about 3 nm. In another embodiment, the macromolecular peptide aggregate is about 1 nm in diameter. In yet another embodiment, the macromolecular peptide aggregate is between 0 and about 1 nm in diameter.

Systemic Immunity

The present invention also features methods of administering a macromolecular peptide aggregate to a mammal for the purpose of providing systemic immunity. This is because it has been shown for the first time herein that administration to a mammal of a macromolecular peptide aggregate, wherein the aggregate has certain physical properties, can engender a systemic immune response in a mammal. As would be understood by one of skill in the art based on the disclosure provided herein, it is desirable to stimulate a systemic immune response in a mammal when immunity to an antigen or to several antigens is desired. Such conditions include, but are not limited to general immunization, immunization boosters, and the like.

Therefore, it is an object of the present invention to provide a method of administering a macromolecular peptide aggregate to a mammal to engender systemic immunity. In an embodiment of the invention, a macromolecular peptide aggregate is transmucosally administered to a mammal. Upon administration of the peptide antigen, the peptide is taken up by the mucosa with which the peptide antigen is in proximity. In this embodiment, the uptake of the peptide antigen engenders systemic immunity in the mammal.

In an aspect of the invention, the peptide macromolecular aggregate responsible for engendering a low-dose response is a complex comprising at least 10 subunits of the peptide. This is because it has been shown for the first time herein that macromolecular peptide aggregates having at least 10 peptide subunits engender systemic immunity in a mammal. Therefore, a method of the present invention includes transmucosal administration of a macromolecular peptide aggregate comprised of at least 10 peptide subunits to a mammal to engender a systemic immunity. In an embodiment of the invention, such a macromolecular peptide aggregate contains about 10 subunits. In another embodiment, such a macromolecular peptide aggregate contains between about 10 subunits and about 15 subunits. In another embodiment, such a macromolecular peptide aggregate contains between about 15 subunits and about 20 subunits. In another embodiment, the macromolecular peptide aggregate contains about 20 subunits. In another embodiment, the macromolecular peptide aggregate preferably contains at least 20 subunits.

In another aspect of the invention, the macromolecular peptide aggregate responsible for engendering systemic immunity is a multiple subunit complex of at least 1 nm in diameter. This is because it has been shown for the first time herein that macromolecular peptide aggregates of at least 1 nm in diameter engender systemic immunity in a mammal. Therefore, a method of the present invention includes transmucosal administration of a macromolecular peptide aggregate of at least 1 nm in diameter to a mammal to engender systemic immunity. In an embodiment of the invention, a macromolecular peptide aggregate is about 1 nm in diameter. In another embodiment, such a macromolecular peptide aggregate is between about 1 nm and about 3 nm. In another embodiment, such a macromolecular peptide aggregate is between about 3 nm and about 5 nm. In another embodiment, the macromolecular peptide aggregate is about 5 nm in diameter. Preferably, in yet another embodiment, the macromolecular peptide aggregate is at least 5 nm in diameter.

The present invention further features a macromolecular peptide aggregate having a molecular weight in excess of 1,000 kDa. It has also been shown for the first time herein that, surprisingly, macromolecular peptide aggregates having a molecular weight in excess of 1,000 kDa engender systemic immunity in a mammal. While not wishing to be bound by any particular theory, this effect is due in part to the physical characteristics of a macromolecular peptide aggregate with a molecular weight in excess of 1,000 kDa.

Therefore, an embodiment of the invention provides a method for engendering a systemic immune response in a mammal. In this embodiment, a macromolecular peptide aggregate with a molecular weight in excess of 1,000 kDa is administered to a mammal transmucosally, resulting in the stimulation of systemic immunity. As described in greater detail elsewhere herein, the administration of a macromolecular peptide aggregate in close proximity with the mucosa results in the uptake of the aggregate by the local mucosa with which the macromolecular peptide aggregate is in proximity. The administration of a macromolecular peptide aggregate with a molecular weight in excess of 1,000 kDa in close proximity with the mucosa of a mammal will be understood by one skilled in the art, based on the disclosure provided herein, to result in the uptake of such an aggregate by the mucosa. Methods of uptake of substances by the mucosa are well-known to one of skill in the art and are therefore not discussed herein.

As described in detail above, it has been disclosed herein for the first time that, by way of several non-limiting examples, a macromolecular peptide aggregate having at least 20 peptide subunits, or having a diameter of at least 5 nm, or having a molecular weight of at least 1,000 kDa can engender a systemic immune response in a mammal upon transmucosal administration of such a macromolecular peptide aggregate. However, the present invention also encompasses methods of administration of a macromolecular peptide aggregate to a mammal with the purpose of engendering a systemic immune response, wherein the macromolecular peptide aggregate has more than one of the physical characteristics set forth herein. In an embodiment of the invention, a macromolecular peptide aggregate having at least 20 peptide subunits and having a molecular weight of at least 1,000 kDa is transmucosally administered to a mammal. Transmucosal administration of such an aggregate to a mammal engenders systemic immunity. As will be understood by one of skill in the art based on the disclosure provided herein, transmucosal administration to a mammal of a macromolecular peptide aggregate having more than one of the physical characteristics described herein, wherein such physical characteristics each dictate that such aggregates engender systemic immunity in a mammal, engenders systemic immunity in the mammal.

In an aspect of the present invention, a method is provided for transmucosal administration of a macromolecular peptide aggregate of a hepatitis B viral surface protein. In this aspect of the invention, a hepatitis B viral surface protein macromolecular aggregate is administered to a mammal transmucosally, taken up by the local mucosa as described elsewhere herein, and engenders systemic immunity in the mammal. This is because, as has disclosed for the first time herein and described in greater detail elsewhere herein, the transmucosal administration to a mammal of a macromolecular aggregate of a hepatitis B viral surface protein engenders a systemic immune response in the mammal.

Therefore, it is an object of the present invention to provide systemic immunity against a hepatitis B virus. As described by Arntzen et al. (1996, PNAS 93(11):5335-40) and Kong et al. (2001, PNAS 98(20):11539-44.), both of which are incorporated by reference herein in their entirety, hepatitis B remains a worldwide health concern. Though the current injectable hepatitis B vaccine is functional, a less expensive, easier to administer vaccine can make significant progress towards immunization of individuals against hepatitis B worldwide. In the present invention, it is disclosed how an oral hepatitis B vaccine is made and used in order to engender systemic immunity against hepatitis B. In particular, and surprisingly, macromolecular aggregates of hepatitis B viral surface protein, hepatitis B viral nucleocapsid protein, and hepatitis B viral envelope protein administered according to a method of the present invention are useful for inducing systemic immunity in a mammal.

In one embodiment of the present invention, an administered macromolecular aggregate of a hepatitis B viral surface protein is comprised of at least 10 protein subunits. In another embodiment of the invention, an administered macromolecular aggregate of a hepatitis B viral surface protein is comprised of at least 20 protein subunits. In another embodiment of the invention, an administered macromolecular aggregate of a hepatitis B viral surface protein has a molecular weight of at least 1,000 kDa. In yet another embodiment of the present invention, an administered macromolecular aggregate of a hepatitis B viral surface protein has a molecular weight of at least 1,000 kDa and is comprised of at least 20 protein subunits.

In an embodiment of the invention, an administered macromolecular aggregate of a hepatitis B viral surface protein has a diameter of at least 1 nm. In another embodiment of the invention, an administered macromolecular aggregate of a hepatitis B viral surface protein has a diameter of at least 5 nm.

In another aspect of the present invention, a method is provided for transmucosal administration of a macromolecular peptide aggregate of a hepatitis B viral nucleocapsid protein. In this aspect of the invention, a hepatitis B viral nucleocapsid protein macromolecular aggregate is administered to a mammal transmucosally, taken up by the local mucosa as described elsewhere herein, and engenders systemic immunity in the mammal. In one embodiment of the invention, an administered macromolecular aggregate of a hepatitis B viral nucleocapsid protein is comprised of at least 10 protein subunits. In another embodiment of the invention, an administered macromolecular aggregate of a hepatitis B viral nucleocapsid protein is comprised of at least 20 protein subunits. In another embodiment of the invention, an administered macromolecular aggregate of a hepatitis B viral nucleocapsid protein has a molecular weight of at least 1,000 kDa. In yet another embodiment of the present invention, an administered macromolecular aggregate of a hepatitis B viral nucleocapsid protein has a molecular weight of at least 1,000 kDa and is comprised of at least 20 protein subunits.

In an embodiment of the invention, an administered macromolecular aggregate of a hepatitis B viral nucleocapsid protein has a diameter of at least 1 nm. In another embodiment of the invention, an administered macromolecular aggregate of a hepatitis B viral nucleocapsid protein has a diameter of at least 5 nm.

In yet another aspect of the present invention, a method is provided for transmucosal administration of a macromolecular peptide aggregate of a hepatitis B viral envelope protein. In this aspect of the invention, a hepatitis B viral envelope protein macromolecular aggregate is administered to a mammal transmucosally, taken up by the local mucosa as described elsewhere herein, and engenders systemic immunity in the mammal. In one embodiment of the invention, an administered macromolecular aggregate of a hepatitis B viral envelope protein is comprised of at least 10 protein subunits. In another embodiment of the invention, an administered macromolecular aggregate of a hepatitis B viral envelope protein is comprised of at least 20 protein subunits. In another embodiment of the invention, an administered macromolecular aggregate of a hepatitis B viral envelope protein has a molecular weight of at least 1,000 kDa. In yet another embodiment of the present invention, an administered macromolecular aggregate of a hepatitis B viral envelope protein has a molecular weight of at least 1,000 kDa and is comprised of at least 20 protein subunits.

In an embodiment of the invention, an administered macromolecular aggregate of a hepatitis B viral envelope protein has a diameter of at least 1 nm. In another embodiment of the invention, an administered macromolecular aggregate of a hepatitis B viral envelope protein has a diameter of at least 5 nm.

Methods and routes of administration of a macromolecular peptide aggregate of the present invention to a mammal would be understood by one of skill in the art, and are more fully described elsewhere herein.

The present invention also features methods for administering a macromolecular peptide aggregate; wherein a peptide aggregate is comprised of a peptide isolated from a natural source, a recombinantly produced peptide, a recombinantly modified peptide, a synthetically produced peptide, or a chemically modified peptide. Therefore, the present invention also provides for methods comprising analogs of a protein or peptide which comprises a macromolecular peptide aggregate useful for engendering mucosal and/or systemic immunity as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine;

Modifications (which do not normally alter primary sequence) include in vivo, or in vitro, chemical derivatization of peptides, e.g., acetylation, or carboxylation, or other such chemical treatment. Such chemical modification of peptides is well-known to the skilled artisan, and is therefore not discussed here further. Also included are modifications of glycosylation, e.g., those made by modifying the glycosylation patterns of a peptide during its synthesis and processing or in further processing steps e.g., by exposing the peptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are macromolecular peptide aggregates, the peptide subunits of which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of a protein or peptide which comprises a macromolecular peptide aggregate useful for engendering mucosal and/or systemic immunity (or of the DNA encoding the same) which mutants, derivatives and variants are peptides which are altered in one or more amino acids (or, when referring to the nucleotide sequence encoding the same, are altered in one or more base pairs) such that the resulting peptide (or DNA) is not identical to the wild type sequences of the peptide subunits, for example, but has the same biological property as the wild type peptide subunit, in that the peptide has biological/biochemical properties of the wild type subunit as known to one of skill in the art.

Further, the invention should be construed to include naturally occurring variants or recombinantly derived mutants or fragments of a protein or peptide which comprises a macromolecular peptide aggregate useful for engendering mucosal and/or systemic immunity, which variants, mutants or fragments render the protein encoded thereby either more, less, or just as biologically active as the full-length proteins and/or the truncated proteins of the invention.

In addition, the skilled artisan would appreciate that changes can be introduced by mutation of the nucleic acid encoding the protein thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

To generate variant proteins, an isolated nucleic acid molecule encoding a variant protein can be created by introducing one or more nucleotide substitutions, additions or deletions into the nucleotide sequence of any protein or peptide which comprises a macromolecular peptide aggregate useful for engendering mucosal and/or systemic immunity, such that one or more amino acid residue substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The invention therefore also features a macromolecular peptide aggregate that is stabilized in the aggregate form by recombinant protein engineering of the peptide. Such a macromolecular peptide aggregate is useful in a method of the invention designed to engender either systemic immunity, oral tolerance, or both. As will be understood by one of skill in the art when armed with the present disclosure, mutations can be designed or inserted into a peptide for the subsequent purpose of joining or linking one or more protein subunits together. Such modifications to a peptide include, but are not limited to, one or more site-directed amino acid mutations, incorporation of one or more unnatural amino acids, deletion of one or more amino acids, post-translational in vivo or in vitro enzymatic modifications to a peptide, post-translational in vivo or in vitro chemical modifications to a peptide, and environmentally-induced structural changes to the peptide.

The invention also features a macromolecular peptide aggregate that is stabilized in the aggregate form by chemical treatment of the peptide. Such a macromolecular peptide aggregate is useful in a method of the invention designed to engender either systemic immunity, oral tolerance, or both. As will be understood by one of skill in the art when armed with the present disclosure, chemical treatment of the peptide includes, but is not limited to, techniques using such compounds as thiol group modifying regents, amino group modifying reagents, carboxyl group modifying reagents, chemical crosslinkers, cleavable chemical crosslinkers, reagents that react with specific amino acids, reagents that randomly modify peptidyl amino acids, and other such reagents known to one skilled in the art.

It will be appreciated that more than one modification to a peptide may be employed in order to produce a desired macromolecular peptide aggregate useful in a method of the present invention. By way of a non-limiting example, a macromolecular peptide aggregate may be stabilized in part by the recombinant introduction of a point mutation in the peptide sequence, wherein the point mutation allows to peptide subunits to covalently associate with one another. The recombinantly-modified, associated two-peptide aggregate may be further stabilized by means of chemical modification of one or more amino acid side chains in one or more peptide subunits. A chemically-modified side chain, when in proximity with another similarly-modified side chain, can react with the similarly-modified side chain, forming a covalent linkage between the two peptide subunits on which the chemically-modified side chains exist. Accordingly, the two peptide subunits can be stabilized concomitantly by two means—recombinant protein chemistry and chemical treatment.

Therefore, the present invention provides an embodiment in which a macromolecular peptide aggregate is stabilized in aggregate form by means of recombinantly-introduced mutations to the peptide subunit. In another embodiment of the invention, a macromolecular peptide aggregate is stabilized in aggregate form by means of recombinantly-introduced mutations to the peptide subunits and chemical treatment of the peptide subunits. It will be understood that stabilization of a macromolecular peptide aggregate of the present invention can be effected by a single means, or that stabilization of a macromolecular peptide aggregate of the present invention can be effected by multiple means, such means being disclosed in detail elsewhere herein. When multiple means are used to stabilize a macromolecular peptide aggregate of the invention, one of skill in the art will understand that such means may be designed to work in concert, or that such means may function independently of one another.

It will be understood that stabilized macromolecular complexes of the present invention may be useful in the induction of oral tolerance, local immunity, or systemic immunity, as described in greater detail elsewhere herein, and that methods of producing a stabilized macromolecular peptide aggregate a set forth regarding the discussion of methods of engendering systemic immunity apply equally and with equal force to the production of stabilized macromolecular peptide aggregates useful in methods of the induction of oral and mucosal tolerance.

One of skill in the art will understand, based on the disclosure herein, how to assay a macromolecular peptide aggregate to ascertain the physical form of the aggregate. That is, upon production of a stabilized macromolecular peptide aggregate of the invention, one of skill in the art will understand how to determine the diameter, the number of subunits, and the molecular weight of the stabilized macromolecular peptide aggregate. For example, the molecular weight of a stabilized macromolecular peptide aggregate of the invention can be determined using gel filtration column chromatography, fluorescence spectroscopy, mass spectrometry, and gel electrophoresis, among other techniques. The number of subunits comprising a stabilized macromolecular peptide aggregate of the invention can be determined using gel filtration, fluorescence spectroscopy, mass spectrometry, and amino acid analysis, among other techniques. And the radius of a stabilized macromolecular peptide aggregate of the invention can be determined using sucrose density gradient centrifugation, analytical ultracentrifugation, and fluorescence spectroscopy, among other techniques. The aforementioned techniques are not intended to be an exhaustive list of available analytical techniques, as will be understood by the skilled artisan.

The present invention also features methods of inducing oral tolerance, wherein a transmucosally administered peptide is administered to a mammal in a monomolecular physical form. As discussed in greater detail elsewhere herein, a monomolecular peptide is useful for the induction of oral tolerance without inducing systemic immunity when such induction of systemic immunity is undesirable. Such conditions include, but are not limited to, patient suffering from chronic infections and other chronic illnesses.

In an embodiment of the invention, a monomolecular peptide species of the invention is produced by disrupting a macromolecular peptide aggregate or other such macromolecular peptide species. Means of disruption of oligomeric protein structures are well known to those of the art, and include the use of techniques such as high salt concentrations, chaotropic agents, detergents, accessory binding proteins, serum albumin, sonic disruption, heat, cold, dilution, and the like. In another embodiment of the invention, a monomolecular peptide species of the invention is stabilized by treatment of the monomolecular peptide species. Such techniques include, but are not limited to, high salt concentrations, chaotropic agents, detergents, accessory binding proteins, serum albumin, sonic disruption, heat, cold, dilution, chemical modification of the peptide, and contacting a monomolecular peptide species with an affinity binding reagent.

In yet another embodiment of the invention, a monomolecular peptide species of the invention is produced using recombinant molecular biology techniques. As will be understood by one of skill in the art when armed with the present disclosure, such monomolecular peptide species can be produced using site-directed mutagenesis techniques, including substitution of one or more amino acid residues, deletion of one or more amino acid residues, addition of one or more amino acid residues, fusion of two or more proteins, incorporation of one or more unnatural amino acid residues, among others.

In an embodiment of the invention, a hepatitis B viral nucleocapsid protein is transmucosally administered to a mammal to engender oral tolerance. In this embodiment, a hepatitis B viral nucleocapsid protein is altered using recombinant molecular biology techniques to provide a mutant hepatitis B viral nucleocapsid protein that does not self-associate to form an oligomer, as described in greater detail elsewhere herein. Briefly, the amino terminus of a hepatitis B viral nucleocapsid protein is genetically altered to contain an additional seven amino acids normally found in the precursor sequence of hepatitis B viral nucleocapsid protein for the purpose of enhancing solubility of the hepatitis B viral nucleocapsid protein and producing a protein resistant to oligomer formation.

Antigens and Epitopes Useful in the Invention

It is also a feature of the present invention to provide any antigen known to one of skill in the art to be useful in the induction of oral tolerance, local immunity, or systemic immunity. By way of a non-limiting example, such antigens include an antigen from an infectious agent and a cancer antigen, among others. Using methods and compositions disclosed in the present invention, one of skill in the art will understand the physical characteristics of a peptide required to effect a desired modulation of the immune system in a mammal. Therefore, a macromolecular peptide aggregate or a monomolecular peptide species comprises an antigen as set forth in the present invention. It is known that, in some cases, an entire antigenic molecule comprises an epitope, and is responsible for the development of immunity in a mammal. It is also known that, in other cases, a specific portion or specific portions of antigenic molecules forms a relevant epitope, and is responsible for the induction of immunity in a mammal. The present invention, in part, encompasses both of these possibilities.

In one embodiment, a method of the invention comprises modulating an immune response of a mammal by transmucosally administering to the mammal a composition comprising an antigen or epitope which is located in close proximity to the immune response. One aspect of the invention, comprising orally administering the composition, is herein alternately designated "oral antigen tolerization therapy" or "induction of oral tolerance." An embodiment of the invention provides a method of inducing oral tolerance in a mammal, wherein the administered antigen or epitope is monomolecular in physical form. Another embodiment of the invention provides a method of inducing oral tolerance in a mammal, wherein the administered antigen or epitope is macromolecular form. Macromolecular forms of antigens or epitopes useful in this embodiment of the invention are discussed in greater detail elsewhere herein.

Recent studies suggest that the pathological consequences of chronic infections of mammals by various infectious agents may be the result of a low, persistent immune response elicited by the presence of the infectious agent in the mammal. It has been discovered that symptoms exhibited by mammals chronically infected with an infectious agent may be improved by modulation of the persistent agent-induced immune response in the mammal. Modulation of the immune response will not have deleterious consequences in a mammal infected with an infectious agent which is non-pathogenic. Furthermore, where the infectious agent exhibits limited pathogenicity but the immune response to the infectious agent causes more significant pathogenicity, it is desirable to ablate the pathogenicity caused by the immune response by modulating that immune response, even though the pathogenicity attributable to the infectious agent remains.

By way of a non-limiting example, it has been reported that essentially 100% of the liver cells of a chronically HBV-infected human contain replication competent virus. Thus, the immune response to the virus apparently does not control the spread of HBV in the patient. Furthermore, HBV is not directly pathogenic to liver cells. Instead, the immune response of the patient to the presence of HBV causes damage to the liver cells. Therefore, HBV infection is an example of infection of a mammalian cell with an infectious agent wherein the infectious agent exhibits limited pathogenicity but the immune response to the infectious agent causes more significant pathogenicity.

Similarly, HIV-1 does not directly damage host T lymphocytes in a human infected with HIV-1. Instead, the T lymphocytes are killed by the immune system through the action of cytotoxic lymphocytes which are activated in response to HIV-1 infection. Other chronic infectious agents which do not themselves damage the tissue of a human host, but which result in host-mediated damage to itself include HTLV-I, *Mycobacterium tuberculosis, Leishmania donovani*, group. B hemolytic *Streptococcus* species, *Trypanosoma cruzi, Onchocerca volvulus, T. braziliensis*, and *S. mutans.*

Thus, it is highly desirable to modulate the immune response of a mammal which is elicited in response to certain chronic infections. In particular, it is highly desirable to modulate the immune response of a human which is elicited in response to certain infectious agents including, but not limited to, those described herein.

An embodiment of the invention includes a method comprising transmucosal administration of one or more therapeutic epitopes to a mammal. Transmucosal administration of an epitope may be accomplished by delivering the epitope to a mammal orally, enterally, intranasally, by a pulmonary route, colonically, or by any other known transmucosal delivery route. Colonic administration, as used herein, means administration to any portion of the large intestine, such as by rectal administration. Oral administration which does not bypass the stomach is preferred. For inhalation methods, treatment is preferably through the bronchial and pulmonary mucosa.

A method of the present invention includes both prophylactic treatment measures which prevent damage caused by the immune response elicited in response to a chronic infection and therapeutic treatment measures which ameliorate clinical symptoms resulting from damage caused by this immune response. Any clinically or statistically significant attenuation of even one symptom associated with a an undesirable immune response following treatment in accordance with the method of the present invention is included within the scope of the invention. By way of example, increased liver size, the presence of tumors and ascites, elevated serum levels, of alpha-feto-protein, fever, and pain, are associated with hepatocellular carcinoma associated with chronic HBV infection in a human. Amelioration or elimination of one or more these symptoms using the methods described herein is within the scope of the present invention.

Prophylactic treatment according to a method of the present invention includes, but is no limited to, transmucosal administration of an epitope of an infectious agent to a mammal prior to infection of the mammal with the infectious agent, transmucosal administration of an epitope of an infectious agent to the mammal following infection of the mammal with the infectious agent but prior to exhibition of an undesirable immune response of the mammal elicited by such infection, transmucosal administration to the mammal of an epitope displayed by a tissue of the mammal prior to infection of the mammal with the infectious agent, transmucosal administration to the mammal of an epitope displayed by a tissue of the mammal following infection of the mammal with the infectious agent but prior to exhibition of an undesirable immune response of the mammal elicited by such infection, and the like.

Therapeutic treatment according to a method of the present invention includes, but is not limited to, transmucosal administration of either an epitope of an infectious agent or an epitope displayed by a tissue of the mammal following infection of the mammal with the infectious agent and exhibition by the mammal of an undesirable immune response elicited by such infection.

It is contemplated that the invention is operable when used in conjunction with traditional therapies aimed at suppressing replication of an infectious agent and reinfection of cells or tissues of the host by that agent. By way of a non-limiting example, chronic HBV infection may be treated by simultaneously using the method described herein and administering lamivudine to a human patient.

In accordance with a method of the present invention, an epitope is administered transmucosally to a mammal which is chronically infected with an infectious agent and which exhibits a symptom of an autoimmune response, thereby inducing antigenic tolerance of the immune system of the mammal for the epitope and modulating the immune response elicited by the mammal in response to the presence of the agent.

Epitopes which may be administered to a mammalian host according to a method of the present invention include, but are not limited to, an epitope of an antigen derived from the infectious agent, an epitope of an antigen which is displayed by a tissue in the mammal and which cross-reacts with a component of the host immune response, such as an antibody or a cytotoxic T lymphocyte, which is activated in response to the presence of the infectious agent, a molecule which comprises an epitope recognized by a component of the host immune response which is activated in response to the presence of the infectious agent, a molecule which comprises an epitope located in close proximity in vivo to an epitope which is displayed by a tissue in the mammal and which cross-reacts with a component of the host immune response which is activated in response to the presence of the infectious agent, and a molecule which comprises an epitope recognized by a component of the host immune response which is activated in response to the presence of the infectious agent.

Numerous methods of isolating and preparing epitopes have been described in the literature. Methods of identifying epitopes of an antigen and methods of preparing molecules comprising an identified epitope of an antigen are known in the art. The epitope which is useful in the method of the invention includes any epitope which, when transmucosally administered to a mammal, induces immune tolerance toward the epitope in the mammal. It is contemplated that any epitope of any infectious agent which induces an undesirable immune response in a mammal infected with the agent is useful in the method of the invention. It is furthermore contemplated that any epitope which is normally displayed by a tissue of such an infected mammal and which is either identical to or located in close proximity to an epitope which cross-reacts with a component of the host immune response which is activated in response to the presence of the infectious agent is useful in the method of the invention.

Thus, by way of a non-limiting example, an epitope may be administered to a human patient according to the method of the invention for treatment of rheumatic fever which develops in response to infection of a patient with a group B *Streptococcus* bacterium. Such a patient develops antibodies and reactive T cells to bacterial antigens which cross-react with a normal tissue antigen present in the synovium of the joints of the patient. If the bacterial epitope is orally administered to the patient, the patient will develop epitope-specific immune hyporesponsiveness, and destruction of tissues in the patient's joints will be suppressed. Similarly, if the tissue antigen is orally administered to the patient, the inflammatory reaction in the patient will be abrogated or significantly attenuated. In addition, the method of the invention may be practiced by administering to the patient an epitope which is normally expressed in close proximity to the tissue antigen or one which is displayed by a tissue in close proximity to the tissue antigen following infection of the patient by the bacterium. Thus, by way of example, an epitope which is normally expressed in the synovium of the joints of the patient and which is different from the tissue antigen may be administered to the patient according to the method of the invention to alleviate arthritis caused by the autoimmune response elicited in response to the presence of the bacterium.

Examples, of epitopes which may be administered to a human chronically infected with HBV include, but are not limited to, an epitope of the HBV viral coat protein designated HBsAg, an epitope of the HBV core protein, or an epitope of the protein encoded by the X gene of HBV.

Infectious agents which elicit host immune responses against which the methods of the present invention are effective include, but are not limited to viral, bacterial, and parasitic infectious agents such as HBV, hepatitis C virus, parvovirus B19, Borna disease virus, HIV, HTLV-1, *Mycobacterium tuberculosis*, a group B hemolytic *Streptococcus bacterium, S. mutans, Trypanosoma cruzi, Leishmania donovani, Onchocerca volvulus, T. braziziensis*, and *S. mansoni*.

Epitopes useful in the method of the invention include epitopes which possess the ability to elicit production of immune-suppressing cells following transmucosal administration of the epitope. Such immune-suppressing cells are characterized by the fact that they secrete immunosuppressive factors such as TGF-.beta. and IL-10 and that they have the ability to migrate to anatomical sites of persistent immune reactivity. Thus, symptoms of autoimmune reactions elicited in response to the presence in a host mammal of an infectious agent may be relieved by administering to the mammal an epitope which induces immune-suppressive cells and which is not expressed by the agent. Such epitopes may be expected to have broad applicability to modulate autoimmune responses elicited by a variety of infectious agents.

The epitope of a molecule administered according to the method of the invention may be an epitope located on an antigen of the infectious agent, or an epitope located on a tissue antigen of the mammal. When the epitope is an epitope located on a tissue antigen of the mammal, the tissue antigen may be a tissue antigen which does not normally react with a component of the immune system of the mammal, but which reacts with the component when the mammal is infected by the infectious agent.

Methods of Suppressing an Immune Response

The present invention also features methods of suppressing an immune response in a host. As described in detail elsewhere herein, in the cases of certain chronic infections in mammals, it may be desirable to suppress the appearance of further immune response, or to suppress an existing immune response. The present invention, in part, meets this need. That is because it has been shown herein that transmucosal administration of monomolecular or low molecular weight peptide species suppresses an immune response in a mammal.

In an embodiment of the invention, a peptide is transmucosally administered to a mammal. Upon administration of the peptide antigen, the peptide is taken up by the mucosa with which the peptide antigen is in proximity. In this embodiment, the uptake of the peptide antigen suppresses an immune response in the mammal. Therefore, a method of the present invention includes transmucosal administration of a macromolecular peptide aggregate to a mammal to suppress an immune response in the mammal.

In one aspect of the invention, the peptide is a monomolecular species. In an embodiment of the invention, the monomolecular species represents the naturally-occurring form of the peptide. In a non-limiting example, a peptide useful in the invention may be isolated from a naturally-occurring source. In another non-limiting example of the invention, a peptide may be synthetic. In yet another non-limiting example, a peptide of the invention may be produced by recombinant techniques. A monomolecular peptide of the invention may therefore be designed to exist in a monomolecular physical form.

In an aspect of the present invention, a method is provided for transmucosal administration of a monomolecular peptide of a hepatitis B viral surface protein. In this aspect of the invention, a hepatitis B viral surface protein monomolecular peptide is administered to a mammal transmucosally, taken up by the local mucosa as described elsewhere herein, whereby the peptide suppress an immune response in the mammal. This is because, as has been disclosed for the first time herein and described in greater detail elsewhere herein, the transmucosal administration to a mammal of a monomolecular peptide of a hepatitis B viral surface protein suppresses an immune response in a mammal.

As disclosed elsewhere herein, the suppression of an immune response in a mammal is useful in situations including, but not limited to, treatment of chronic infection in a mammal. Surprisingly, monomolecular peptides of hepatitis B viral surface protein, hepatitis B viral nucleocapsid protein, or hepatitis B viral envelope protein, administered according to a method of the present invention, are useful for suppressing an immune response in a mammal.

The present invention also features methods of administration of low-molecular weight complexes of hepatitis B viral surface protein, hepatitis B viral nucleocapsid protein, or hepatitis B viral envelope protein for suppressing an immune response in a mammal. As described in greater detail in the Experimental Examples, certain low molecular weight peptide complexes, surprisingly, are useful in suppressing an immune response in a mammal.

In one embodiment of the present invention, an administered low molecular weight peptide complex of a hepatitis B viral surface protein is comprised of fewer than 10 peptide subunits. In another embodiment of the invention, an administered low molecular weight peptide complex of a hepatitis B viral surface protein is comprised of fewer than 5 peptide subunits. In another embodiment of the invention, an administered low molecular weight peptide complex of a hepatitis B viral surface protein has a molecular weight of less than 1,000 kDa. In yet another embodiment of the present invention, an administered low molecular weight peptide complex of a hepatitis B viral surface protein has a molecular weight of less than 1,000 kDa and is comprised of fewer than 10 protein subunits. In another embodiment of the invention, an administered low molecular weight peptide complex of a hepatitis B viral surface protein has a diameter of less than 1 nm.

In one embodiment of the present invention, an administered low molecular weight peptide complex of a hepatitis B viral nucleocapsid protein is comprised of fewer than 10 peptide subunits. In another embodiment of the invention, an administered low molecular weight peptide complex of a hepatitis B viral nucleocapsid protein is comprised of fewer than 5 peptide subunits. In another embodiment of the invention, an administered low molecular weight peptide complex of a hepatitis B viral nucleocapsid protein has a molecular weight of less than 1,000 kDa. In yet another embodiment of the present invention, an administered low molecular weight peptide complex of a hepatitis B viral nucleocapsid protein has a molecular weight of less than 1,000 kDa and is comprised of fewer than 10 protein subunits. In another embodiment of the invention, an administered low molecular weight peptide complex of a hepatitis B viral nucleocapsid protein has a diameter of less than 1 nm.

In one embodiment of the present invention, an administered low molecular weight peptide complex of a hepatitis B viral envelope protein is comprised of fewer than 10 peptide subunits. In another embodiment of the invention, an administered low molecular weight peptide complex of a hepatitis B viral envelope protein is comprised of fewer than 5 peptide subunits. In another embodiment of the invention, an administered low molecular weight peptide complex of a hepatitis B viral envelope protein has a molecular weight of less than 1,000 kDa. In yet another embodiment of the present invention, an administered low molecular weight peptide complex of a hepatitis B viral envelope protein has a molecular weight of less than 1,000 kDa and is comprised of fewer than 10 protein subunits. In another embodiment of the invention, an administered low molecular weight peptide complex of a hepatitis B. viral envelope protein has a diameter of less than 1 nm.

The present invention also features antigens comprised of macromolecular aggregates comprising non-peptide moieties. A "non-peptide macromolecular aggregate," as the term is used herein, refers to any macromolecular aggregate that is comprised of non-peptide chemical and biochemical moieties, including, but not limited to carbohydrates, lipids, and chemical moieties.

In an embodiment of the present invention, a non-peptide macromolecular aggregate of the present invention is transmucosally administered to a mammal. Upon administration of a non-peptide macromolecular aggregate, the aggregate is taken up by the mucosa with which the aggregate is in proximity. In an embodiment, the administration of such an aggregate engenders systemic immunity in a mammal, as described elsewhere herein. In another embodiment, the administration of such an aggregate engenders oral tolerance in a mammal, as described elsewhere herein. In yet another embodiment, a non-peptide macromolecular aggregate of the invention suppresses an immune response in a mammal, as described elsewhere herein.

The present invention also contemplates antigens comprised of macromolecular aggregates comprising both peptide and non-peptide moieties. In an embodiment of the present invention, a mixed species macromolecular aggregate of the present invention is transmucosally administered to a mammal. Upon administration of a mixed species macromolecular aggregate, the aggregate is taken up by the mucosa with which the aggregate is in proximity. In an embodiment, the administration of a mixed species macromolecular aggregate engenders systemic immunity in a mammal, as described elsewhere herein. In another embodiment, the administration of a mixed species macromolecular aggregate engenders oral tolerance in a mammal, as described elsewhere herein. In yet another embodiment, a mixed species macromolecular aggregate of the invention suppresses an immune response in a mammal, as described elsewhere herein.

Methods of Preparation of an Antigen or Epitope Useful in the Invention

Antigens and epitopes useful in a method of the present invention may be isolated from natural sources using known methods or, alternatively, may be prepared recombinantly. Techniques which are used to transform cells, construct vectors, extract messenger RNA, prepare cDNA libraries, and the like are widely practiced in the art, and practitioners are familiar with standard resource materials which describe specific conditions and procedures (see, e.g. Sambrook et al., 1989, Molecular. Cloning: A Laboratory Manual, Cold Spring Harbor Laboratory, New York; Ausubel et al., 1993, Current Protocols in Molecular Biology Green & Wiley, New York).

Known prokaryotic expression systems may be used to produce epitopes useful in the method of the present invention. Plasmid vectors which contain replication sites and control sequences derived from a species compatible with the host are used. In one such prokaryotic expression system, for example, E. coli is transferred using a derivative of pBR322, a plasmid derived from an E. coli species by Bolivar et al. (1977, Gene 2:95). pBR322 contains genes encoding proteins which confer ampicillin and tetracycline resistance and thus provide markers which can be either retained or destroyed in constructing the desired vector.

Prokaryotic control sequences useful to produce the epitope include, but are not limited to, promoters for transcription initiation such as the beta-lactamase (penicillinase) promoter system, the lactose (lac) promoter systems, the tryptophan (trp) promoter system, and the lambda derived P.sub.L promoter system, operator sequences, and ribosome binding site sequences such as the N-gene ribosome binding site (Chang et al., 1977, Nature 198:1056; Goeddel, et al., 1980, Nucl. Acids Res 8:4057; Shimatoake et al., 1981, Nature 292:128).

Eukaryotic organisms, such as yeast may also be used to produce the epitope used in the method of the invention, using known methods for expressing an exogenous protein in, for example, yeast. Laboratory strains of *Saccharomyces cerevisiae*, Baker's yeast, may be used, although a number of other strains are commonly available.

Vectors suitable for yeast expression include the two micron origin of replication, as well as other vectors described in the art (see, e.g., Broach, 1983, Meth. Enzymol. 101:307; Steinchcomb et al., 1979, Nature 282:39; Tschempe et al., 1980, Gene 10:157; Clark et al., 1983, Meth. Enzymol. 101:300). Control sequences for expression of genes in yeast vectors include promoters for the synthesis of glycolytic enzymes (Hess et al., 1968, J. Adv. Enzyme Req. 7:149; Holland et al., 1978, Biochemistry 17:4900). Additional yeast promoters known in the art include the 3-phosphoglycerate kinase promoter and other glycolytic enzyme promoters such as glyceraldehyde-3-phosphate dehydrogenase, hexokinase, pyruvate decarboxylase promoter, phosphoglycerate mutase, pyruvate kinase, triose phosphate isomerase, phosphoglucose isomerase, and glucokinase promoters (Hitzeman et al., 1980, J. Biol. Chem. 255: 2073). Other promoters, which have the additional advantage of permitting transcription to be controlled by manipulating growth conditions include the promoter regions governing expression of alcohol dehydrogenase 2, isocytochrome C, acid phosphatase, degradative enzymes associated with nitrogen metabolism, and enzymes responsible for maltose and galactose utilization (Holland, supra). It is also believed that terminator sequences are desirable at the 3' end of the coding sequences in the constructs which may be used to generate the epitopes described herein. Such terminators are found in the 3' untranslated region following the coding sequences in yeast-derived genes.

Other useful vectors include those which contain control sequences derived from the enolase-gene-containing plasmid peno46 or the LEU2 gene obtained from YEp13 (Holland et al., 1981, J. Biol Chem 256:1385; Broach et al., 1978, Gene 8:121). Any vector containing a yeast compatible promoter, origin of replication and other control sequences is suitable to generate the components required to practice the method of the invention.

Plant cells including, but not limited to, crop plant cells, may be used as hosts to produce epitopes which are useful in the method of the invention. Control sequences compatible with plant cells such as the nopaline synthase promoter and polyadenylation signal sequences are known (see, e.g. Depicker et al., 1982, J. Mol. Appl. Gen 1:561). In some preferred embodiments, the gene encoding the epitope is under the control of an ethylene responsive promoter such as, for example, the E8 promoter of tomatoes (Lincoln et al., 1988, Mol. Gen. Genet. 212:71-75; Deikman et al., 1988, EMBO J. 7:3315-3320). Thus, selective expression of an epitope may be achieved in this manner.

Insect cells may also be used as hosts to produce epitopes useful for the method of the invention, using methods and cells which are known in the art. To make such cells, a gene encoding the desired epitope is operably incorporated into insect cells using known methods (e.g., Griffiths et al., 1997, Meth. Molec. Biol. 75:427-440).

Depending on the type of host cell used, transformation is accomplished using standard techniques appropriate to such cells. The calcium treatment employing calcium chloride, as described by Cohen (1972, Proc. Natl. Acad. Sci. USA 69:2110), or methods described by Sambrook et al. (1989; Molecular Cloning: A Laboratory Manual, Cold Spring Harbor Laboratory, New York), may be used in the case of prokaryotes or other cells which contain substantial cell wall barriers. Infection with *Agrobacterium tumefaciens* (Shaw et al., 1983, Gene 23:315) is believed to be useful for certain plant cells. Transformation of DNA into yeast may be carried out according to the method of Van Solingen et al. (1977, J. Bacteriol. 130:946) and Hsiao et al. (1979, Proc. Natl. Acad. Sci. USA 76:3829). Genes may be transferred to plant cells using a variety of methods such as *Agrobacterium* plasmid-mediated gene transfer, (Truve et al., 1993, Bio/Technology 11: 1048; Streber et al., 1989, Bio/Technology 7:811; Mullins et al., 1991, Bio/Technology 8:1041; Mante et al., 1991, Bio/Technology 9:853; Dong et al., 1991, Bio/Technology 9:859; Penarrubia, 1992, Bio/Technology 10:561; D'Halluin, 1992, Bio/Technology 10:309) microparticle bombardment, (Vasil et al., 1991, Bio/Technology 9:743; Vasil et al., 1992, Bio/Technology 10:286) electroporation, (Chupeau et al., 1989, Bio/Technology 7:503) liposome fusion, (Deshayes et al., 1985, EMBO J. 4:2731-2737) polyethylene glycol-mediated transformation, (Potrykus et al., Mol. Gen. Genet. 197: 183-188) microinjection, (Griesbach, Biotechnology 3:348-350; Shewmaker, 1986, Mol. Gen. Genet. 202:179-185), viruses (Takematsu et al., EMBO J. 6:307-311), and geminivirus (Ward et al., 1988, EMBO J. 7:1583-1587).

cDNA or genomic libraries may be screened using the colony hybridization procedure. Generally, each microtiter plate is replicated onto duplicate nitrocellulose filter papers (e.g. S&S type BA-85) and colonies are allowed to grow at 37.degree. C. for 14-16 hours on Luria broth agar containing 50 micrograms per milliliter ampicillin. The colonies are lysed and DNA is fixed to the filter by sequential treatment for five minutes with 500 millimolar NaOH, 1.5 molar NaCl, and the filter is washed twice for five minutes each time with 5.times.standard saline citrate (SSC). Filters are air dried and baked at 80.degree. C. for two hours. Duplicate filters are prehybridized at 42.degree. C. for 6-8 hours with ten milliliters per filter of a DNA hybridization buffer, such as one comprising 5.times.SSC adjusted to pH 7.0, 5.times.Denhardt's solution (0.02% (w/v) polyvinylpyrrolidone, 0.02% (w/v) Facial and 0.02% (w/v) bovine serum albumin), 50 mM sodium phosphate buffer adjusted pH 7.0, 0.02% (w/v) SDS, 20 micrograms per milliliter Poly U, and 50 micrograms per milliliter denatured salmon sperm DNA.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating DNA with a suitable restriction enzyme(s) under conditions which are generally understood in the art, and the particulars of which are specified by the manufacturer of these commercially available restriction enzymes (see, e.g., New England Biolabs, Product Catalog). In general, about 1 microgram of plasmid or DNA sequence is cleaved by one unit of enzyme in about 20 microliters of buffer solution. Incubation times of about one hour to two hours at about 37.degree. C. are workable, although variations can be tolerated. After each incubation, protein can be removed by extraction with phenol/chloroform, and may be followed by ether extraction, and the nucleic acid is recovered from aqueous fractions by precipitation with ethanol followed by chromatography using a Sephadex G-5 spin column. If desired, size separation of the cleaved fragments may be performed by polyacrylamide gel or agarose gel electrophoresis using standard techniques. A general description of size separations can be found in Methods in Enzymology (1980, 65:499-560).

Restriction-endonuclease-cleaved fragments may be blunt ended by treating with the large fragment of *E. coli* DNA polymerase I (Klenow) in the presence of the four deoxynucleotide triphosphates (dNTPs) using incubation times of about 15 to 25 minutes at from 20.degree. C. to 25.degree. C. in 50 millimolar Tris buffer at pH 7.6, 50 millimolar NaCl, 6 millimolar MgCl.sub.2, 6 millimolar DTT and 5-10 micromolar dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

In some preferred embodiments of the present invention, expression of a viral coat protein such as a hepatitis B virus surface antigen, or a peptide comprising an epitope thereof, may be achieved in accordance with methods described by Valenzuela et al. (1982, Nature 298:347-350).

Pharmaceutical Compositions

The present invention encompasses the use of a macromolecular peptide aggregate which is useful in a method of the invention, and compositions comprising the aggregate and a pharmaceutically acceptable carrier. The invention also encompasses the use pharmaceutical compositions of an epitope which is useful in a method of the invention, and compositions comprising the epitope and a pharmaceutically acceptable carrier.

As used herein, the term "pharmaceutically acceptable carrier" means a chemical composition with which a macromolecular peptide aggregate or an epitope useful in the method of the invention may be combined and which, following the combination, can be used to administer the macromolecular peptide aggregate or an epitope to a mammal.

A pharmaceutical composition useful for practicing the invention may be administered to deliver a dose of between 1 ng/kg/day and 100 mg/kg/day. In one embodiment, the invention envisions administration of a dose of a macromolecular peptide aggregate or epitope comprising from about 0.1 milligram to about 250 milligrams per day to a human. In another embodiment, the human dose is from about 0.1 milligram to about 25 milligrams per day.

A pharmaceutical composition that is useful in a method of the invention may be administered systemically in oral solid formulations, ophthalmic, suppository, aerosol, topical, powdered, gel, or any other formulation known to be useful for transmucosal delivery of a pharmaceutically active agent. In addition to a macromolecular peptide aggregate or epitope useful in a method of the invention, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer a macromolecular peptide aggregate or epitope according to methods of the invention.

A pharmaceutical composition useful in a method of the invention may further comprise any compound known to be effective for the treatment of infection of a mammal by an infectious agent or may further comprise any known immunosuppressive compound. A pharmaceutical composition may comprise, in addition to a molecule comprising a macromolecular peptide aggregate or epitope described herein, a second molecule selected from the group consisting of an antibiotic, an antiviral compound, an antiparasitic compound, an anti-inflammatory compound, an immunosuppressant, and a synergist. An antibiotic is a composition which kills or inhibits the proliferation of a bacterium. An antiviral compound is a composition which inactivates or inhibits the proliferation of a virus. An antiparasitic compound is a composition which kills or inhibits the proliferation of a parasite. An anti-inflammatory compound is a composition which inhibits or alleviates inflammation in a mammal. An immunosuppressant is a composition which modulates an immune response in a mammal. A synergist is a composition which enhances induction of antigenic tolerance when administered to a mammal in combination with a macromolecular peptide aggregate or epitope.

A pharmaceutical composition useful in a method of the invention may be administered to a mammal in a single dose, in multiple doses, in a continuous or sustained-release formulation, and the like.

Development of antigenic tolerance is dose-dependent over a broad range of dosages. However, it is generally the case that there are minimum and maximum effective dosages. As is understood by one skilled in the art when armed with the disclosure provided herein, effective dosage for a patient suffering from a chronic infection may vary depending upon the form of the epitope. Moreover, the age, sex and Physical condition of the patient, as well as other concurrent treatments being administered also have a bearing on the effective dosage. One skilled in the art would be able to adjust and refine the dosage used and the administration schedules to meet the individual needs of a patient.

Oral tolerance can be induced by employing small or large doses of a macromolecular peptide aggregate or epitope. As set forth in greater detail elsewhere herein, a macromolecular peptide aggregate comprised of fewer than 20 peptide subunits, a macromolecular peptide aggregate of a diameter smaller than 5 nm, a macromolecular peptide aggregate having a molecular weight of less than 1,000 kDa, or a macromolecular peptide aggregate having at least two of the aforementioned characteristics may be useful in engendering oral tolerance in a mammal.

Generally low dosage regimes induce secretion of down regulatory cytokine mediators by regulatory cells. High dosage tolerance, commonly referred to as clonal anergy, employs a passive mechanism in which the clones of cells that are capable of responding to a given epitope are rendered non-responsive due to large concentrations of the epitope which are delivered across the mucosa. In some preferred embodiments of the present invention, low dosage regimes are preferred. Generally, administration to a human of a macromolecular peptide aggregate or epitope in the form of about 0.1 mg to about 250 mg/day of peptide, protein, or glycoprotein will be effective in accordance some methods of the present invention. In other embodiments of the present invention, antigenic tolerance is achieved by administration to a human of amounts of a macromolecular peptide aggregate or epitope, a peptide, protein or glycoprotein ranging from about 0.1 mg to about 25 mg/day.

Synergists may also be used in some embodiments of the present invention to enhance induction of antigenic tolerance. Synergists which have been found to enhance oral tolerance include bacterial lipopolysaccharides from a wide variety of gram negative bacteria such as various subtypes of *E. coli* and *Salmonella* (LPS and Lipid A, Sigma Chemical Co., St Louis, Mo.) and immunoregulatory lipoproteins, such as peptides covalently linked to tripalritoyl-5-glycarylcysteinyl-serylserine (prepared as described in Braun, 1976, Biochim. Biophys. Acta 435:335-337).

Systemic immunity can be induced by employing either small or large doses of a macromolecular peptide aggregate or epitope of the invention. As described elsewhere herein, the present invention also features methods of modulating an immune response by controlling the physical characteristics of an antigen administered to a mammal for the purpose of providing systemic immunity. This is because it, has been shown for the first time herein that administration to a mammal of a macromolecular peptide aggregate, wherein the aggregate has certain physical properties, can engender a systemic immune response in a mammal.

Therefore, as described in greater detail elsewhere herein, transmucosal administration to a mammal of a macromolecular peptide aggregate having certain physical characteristics is useful for engendering systemic immunity. By way of a non-limiting example, such a macromolecular peptide aggregate may have a macromolecular peptide aggregate diameter of at least 5 nm, a macromolecular peptide aggregate molecular weight of at least 1,000 kDa, a macromolecular peptide aggregate containing at least 20 peptide subunits, or a combination of at least two of the aforementioned characteristics. One of skill in the art, when armed with the present disclosure, will readily be able to determine the appropriate dosage of such a macromolecular peptide aggregate to induce systemic immunity in accordance with the present invention.

EXPERIMENTAL EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Example 1

Induction of Mucosal Tolerance by Aggregated Hepatitis B Virus Core Antigen (HBcAg)

Construction, expression, purification and physical characterization of aggregated HBcAg (ag HBcAg). The plasmid pTKHH2 containing a head to tail dimer of the complete genome of hepatitis B virus was treated with EcoR1 endonuclease to cleave at the boundaries of the genome. The resulting digest was phenol/chloroform extracted, and electrophoresed into a 0.5% agarose gel. The 3182 base hepatitis B virus (HBV) genome band of DNA was collected, and the virus core gene was excised using EcoR1 and HindIII. Following phenol/chloroform purification, the product was ligated into the multiple cloning site of pETb 28 (NovaGen). Competent $E.\ coli.$ BL21 cells (NovaGen) were transfected with the plasmid, and colonies were selected based on their resistance to kanamycin. Several colonies were expanded, and minipreps were performed to extract the plasmids. Several plasmids were sequenced and were determined to contain the authentic coding region of the hepatitis B virus core gene. One colony was selected based on its relative expression of HBcAg as determined by western dot blot assay. This clone was expanded in selection broth and the DNA isolated as described previously. A sequence encoding 6 histidines and the T7 peptide was inserted 3' to the HBcAg gene (pET28A vector system, NovaGen) and transformants selected as described. The transgenic protein was expressed by inoculating 50 ml of LB broth with the transgenic bacteria and incubating at 37° C. overnight with shaking. The following morning, the culture was diluted 10 fold with fresh LB containing antibiotics, and when the $OD_{600\ nm}$ reached approximately 0.5, adequate isopropylthiogaloctopyranaside (IPTG) was added to make the culture 1 mM in IPTG. After 2 hours, bacteria were collected by centrifugation, and the pellets were washed once with cold PBS. Bacterial pellets were then resuspended in 8M urea at pH 8.0 and the debris was cleared by centrifugation. The lysed culture was then applied to a column containing Ni-NTA agarose (Qiagen Corporation). The column was washed with 10 volumes of wash buffer as recommended by the supplier, and the product was eluted using a pH 4.5 buffer. Following dialysis against PBS, the purity and identity of the protein was established by PAGE electrophoresis followed by silver staining and western blotting. This protein was found to self-aggregate following dialysis in PBS, yielding a flocculent suspension, and is referred to hereinafter as aggregated HbcAg, as opposed to native HBcAg which assembled into pseudocapsids (Schodel et al., 1993, JBC 268:1332-1337) or modified HBeAg as described elsewhere herein.

Tolerance Induction in Mice

CB17, C3H and C57 BL/6 mice of both sexes were used in these experiments. All animals were between 6 and 14 weeks of age. Mice were immunized with 50 µg native HBcAg particles (nHBcAg) emulsified in an equal volume of Complete Freund's Adjuvant (CFA) on day 36, and received an intraperitoneal booster of HBcAg on day 14.

Control animals were sham inoculated with PBS. On days 2, 4, 6 and 8, selected animals were fed 1 mg or 5 mg of test protein (nHBcAg, aggregated HBcAg or HBeAg as indicated), solubilized in between 0.25 and 0.5 ml of PBS, with a ball point feeding needle. Control animals received an equal volume of PBS. Between days 10 and 17, animals were euthanized and the spleen cells collected and placed in culture in replicates of five. Cells were diluted to contain either $1 \times 10^5$ or $2 \times 10^5$ splenocytes per well in 100 µl of Iscove's medium containing 10% FCS, 50 µg/ml penicillin, 50 µg/ml streptomycin, and $5 \times 10^{-5}$ 2-mercaptoethanol. After 72 and 96 hours, each well received 1 µCi tritiated thymidine, and the incorporated label quantified by scintillography.

Spleen cells collected from immune mice (Immune), or from mice immunized then orally tolerized (Immune/OT) did not significantly proliferate in the absence of antigen in the cultures. When 1 µg per well of HBcAg was supplied, all cells proliferated, but cells from Immune/OT mice underwent mitosis at a significantly lower level. In cultures to which 5 µg of HBcAg had been added, the level of cellular replication was greater still, and the cells isolated from Immune/OT mice again exhibited a significantly depressed proliferation compared to mice not orally fed antigen. Clearly, mucosal presentation of the immunizing antigen after immunity had been established resulted in a dose dependant suppression of the immune response. Data shown are representative of results of at least 6 experiments (FIG. 2).

Example 2

In Vitro Toxicity of HBsAg

Another HBV protein as tested for its ability to induce oral tolerance in alternate physical forms. Recombinant hepatitis B surface antigen existing in 25 nM spheroids (pseudovirions) was purchased from Korea Green Cross. This protein is sold as a vaccine in many countries and has been extensively characterized. It was possible that the recombinant HBsAg obtained might contain contaminants that would adversely affect the growth of immune cells. To test this, the protein was serially diluted to provide concentrations from 3 µg/5 µl to 0.01 µg/5 µl, and was added to replicates of cultures of spleen cells collected from normal mice. Control wells received Con A but no antigen. Cells were stimulated with 5 µg/well of Con A, and were cultured for 4 days. Radioactive thymidine was added to each well, and the cells were cultured for an additional 18 hours. Cells were collected, and their proliferation was quantified by scintillography (FIG. 3).

No statistically significant differences were observed between culture replicates suggesting that the HBsAg was neither toxic nor did it interfere with the proliferation of spleen cells stimulated with a mitogen.

Example 3

Induction of Mucosal Tolerance by HBsAg

Hepatitis B surface antigen (HBsAg) was purchased from Korea Greencross vaccines (Jong Jin City, South Korea). This protein preparation has been shown to consist of predominantly 25 nm spheroids comprised of about 100 subunits of the small HBsAg protein. This particular protein was used in all phases of the HBsAg-requiring experiments. CB17 mice received immunizations of 50 µg of the protein emulsified in Complete Freunds Adjuvant on day 28. All animals received 10 µg of the same protein in PBS as intraperitoneal boosters on day 14. On days 1, 2, 4 and 6, indicated animals were fed 0.1, 1 or 5 mg doses in 0.25 ml of PBS using a ball-tipped feeding needle. Control animals received an equal volume of PBS. The treatments were administered every second day for a total of 4 doses. On day 10, animals were euthanized, and the spleens were aseptically collected. Single cell suspensions were prepared, and dispensed into replicate wells of a 96 well tissue culture cluster. Varying doses of the antigen were added, and the cultures were maintained for 72 hours in 5% $CO_2$/balance air. Each well then received 1 µCi of tritiated thymidine and were cultured for an additional 18 hours. The cells were then collected onto glass fiber filters. Incorporated label was determined by scintillography.

The results of this experiment clearly showed that the oral administration of either of two concentrations of the viral protein resulted in enhanced immune reactivity to the protein in immune animals (FIG. 4). This is in direct contradiction to the preceding experiment in which oral administration of a viral protein resulted in less immune reactivity to the antigen in vitro. To determine whether the physical conformation of the administered antigen was responsible for the booster effect observed, the HBsAg was disrupted by detergent and disulfide bond scission, rapidly renatured, and then tested again for its ability to induce mucosal tolerance.

Example 4

Physiochemical Disruption of HBsAg Pseudovirions

Figure 5:
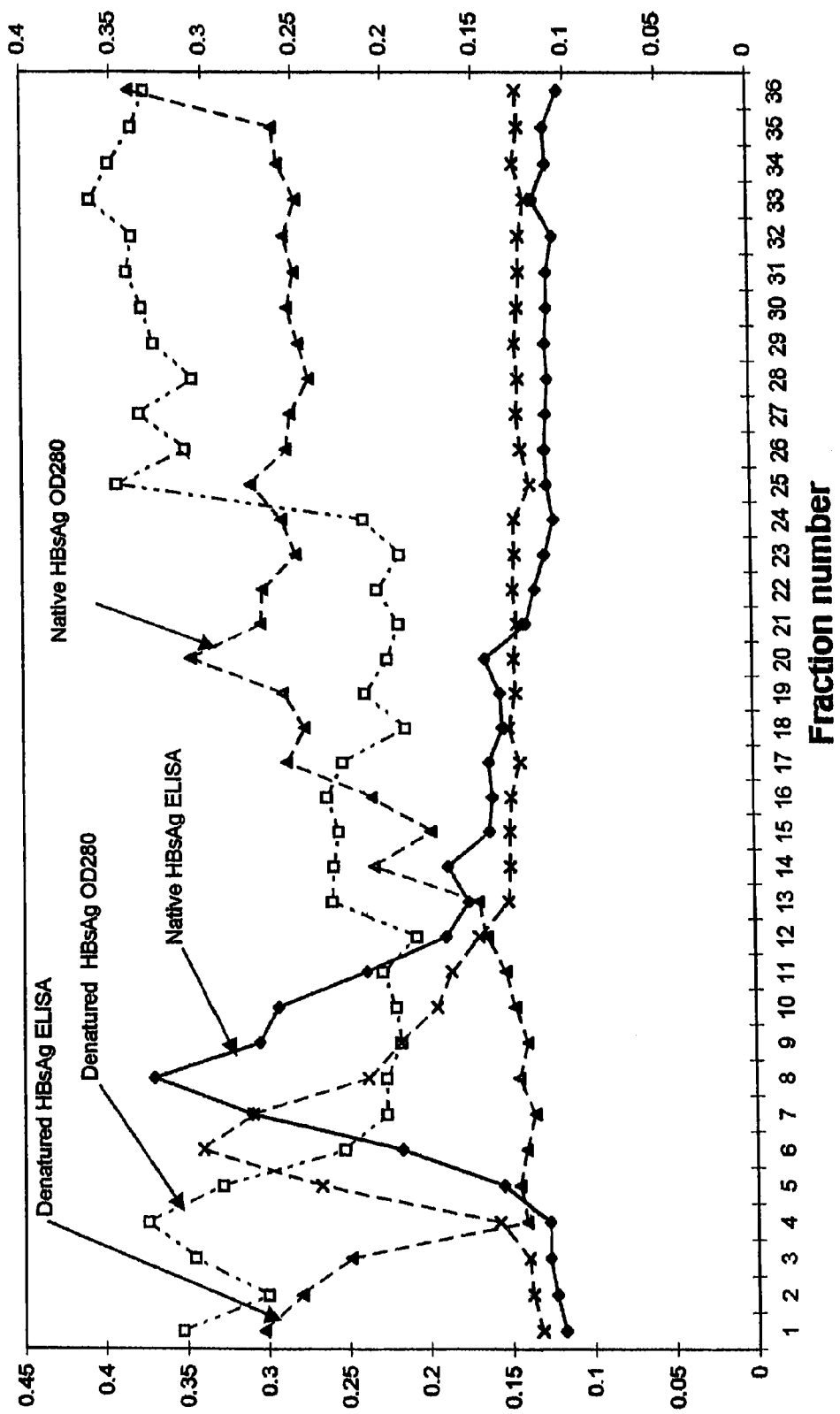
FIG. 5 is a graph depicting the local presence of immune reactive HBsAg at varying densities (sizes) after fractionation on a sucrose density gradient following isopycnic ultracentrifugation. HBsAg was disrupted with 2-mercaptoethanol, 8 M urea and heat. The lysate was applied to a Sepharose G-200 column and fractions were collected while monitoring the $OD_{280\ nm}$. Each fraction was then tested for the presence of immunoreactive HBsAg. Fraction numbers are on the X-axis and $OD_{280\ nm}$ measurements are on the left Y-axis. The OD of the ELISA assay for each fraction is presented on the right Y-axis.

To disrupt the 25 nm HBsAg pseudovirions, an aliquot of the protein was dialyzed against PBS containing 2% SDS and 2% 2-mercaptoethanol overnight at 5° C. then heated to 60° C. for 1 hour. The denatured protein was layered on top of a discontinuous sucrose density gradient consisting of 50%, 40%, 30%, and 20% sucrose in PBS, and then centrifuged for 13 hours at 35,000 RPM in a Beckman SW41 rotor. An aliquot of the non-disrupted native antigen was identically processed. Fractions of 0.30 ml were collected, and optical density at 280 nm and presence of immunoreactive proteins determined for each. Specifically, column eluates were monitored with an flow-through cell mounted in a spectrophotometer adjusted for 280 nm. Immunoreactive protein was determined by transferring 10 µl of each fraction to duplicate wells of a 96 well ELISA plate cluster (Nuncleon), and allowing overnight adhesion at 5° C. Wells were washed with PBS, and unoccupied protein binding sites saturated with 100 µl of 5% powdered milk dissolved in PBS. Following 3 washes with PBS, each well received 50 µl of a 1:5000 dilution of polyclonal rabbit anti-HBsAg for 45 minutes at room temperature. Following washing, all wells were treated with a 1:5000 dilution of goat anti-rabbit Ig that had been conjugated with horseradish peroxidase (Sigma). After an additional 45-minute incubation, all wells were washed with PBS, and 50 µl of 2,4-orthophenylamine diamine/$H_2O_2$ solution (Sigma) was added, and the optical density of each well determined with a microplate ELISA reader at 492 nm. Replicate wells were averaged, and the results were plotted (FIG. 5).

These experiments clearly suggested that the physical size and/or conformation of the protein present in the native preparation, as detected by $OD_{280\ nm}$ protein assay, equilibrated in the denser portions of the gradient. In contrast, proteins recognized by the rabbit antibody specific for HBsAg were present in the lighter fractions. Further, HBsAg disrupted with 2-ME and SDS presented as several immunoreactive peaks including a major band in the lightest fractions.

Example 5

Induction of Mucosal Tolerance by Disrupted HBsAg

Figure 6:
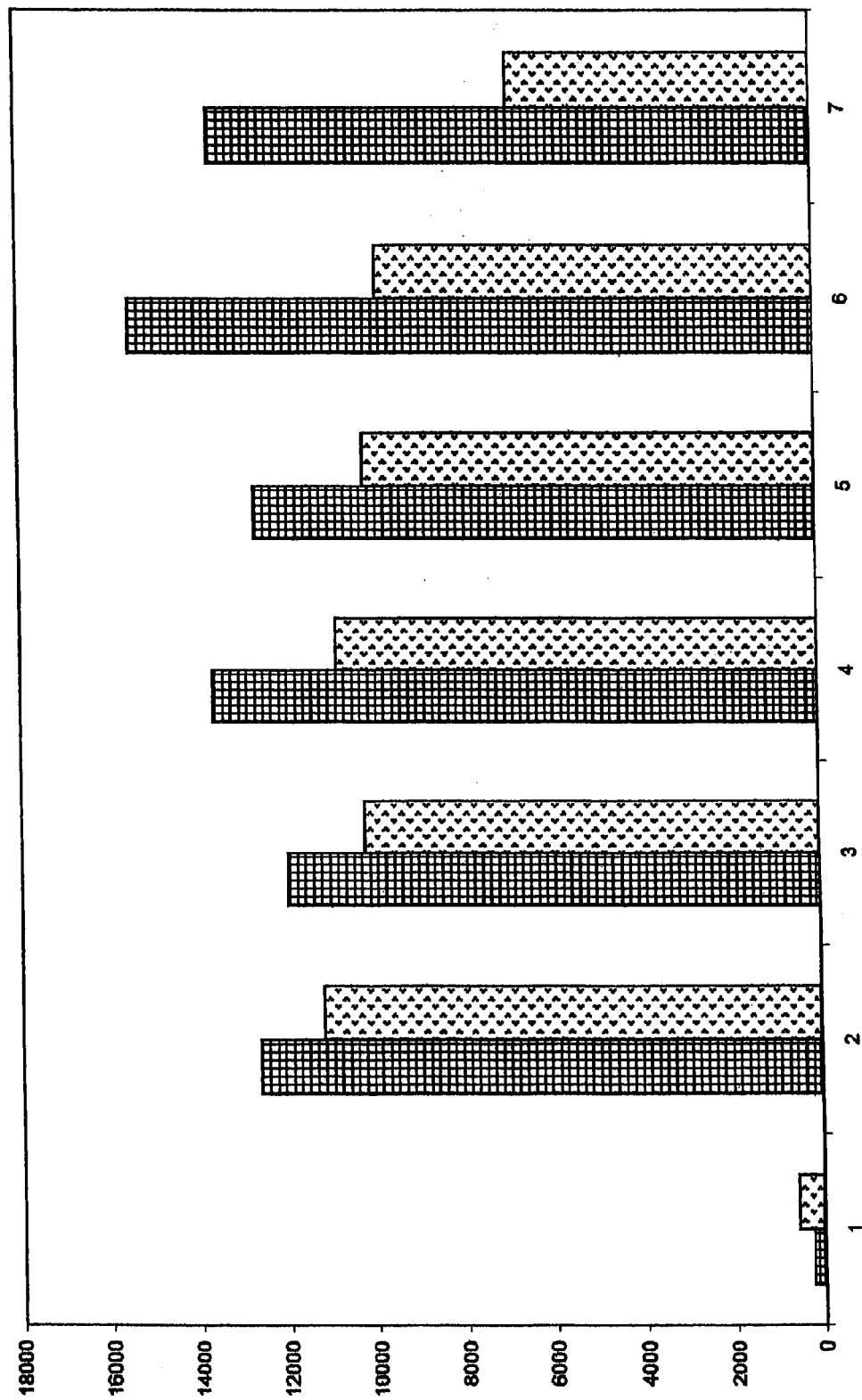
FIG. 6 is a graph illustrating that chemical dissociation of native HBsAg restores the tolerance induction capacity of the antigen. Mice were immunized and boosted as described in Example 5, and some mice were orally tolerized with Pool 1 native antigen (set 2), Pool 1A disrupted antigen (set 3), Pool 2 native HBsAg (set 4) Pool 2A (disrupted HBsAg) (set 5), Pool 3 (Native antigen) or Pool 3A (disrupted HBsAg). Spleen cells were processed for culture, and all cultures challenged with 10 mg of native HBsAg with the exception of set 1 which received no antigenic stimulus. The left axis presents proliferation results measured as CPM.

A 0.5 cm×15 cm chromatography column was loaded with Sephadex G200 (Sigma), which can resolve globular proteins ranging between 20 KD and 200 KD. Approximately 14 mg of denatured HBsAg was applied to the column, and proteins were eluted with PBS. A total of 48 fractions of 0.25 ml each were collected. The protein concentration and immunoreactivity was determined for each, and the fractions were combined into three pools. Pool 1 contained the equivalent of fractions 1-12, Pool 2 contained fractions 13-26, and Pool 3 contained the remainder the fractions. An identical protocol was performed with non-denatured HBsAg. Fraction numbers begin at the bottom of the tube (the highest density and largest aggregates), and three equivalent pools were established: fractions 1-3 for Pool 1A, fractions 4-18 for Pool 2A, and the remainder of the fractions for Pool 3A. The volumes were adjusted to contain 2.5 mg per ml of protein and the samples were then used to determine whether the denatured HBsAg was capable of inducing oral tolerance as opposed to the native protein, which instead had boosted a preexisting immunity. CB 17 mice were immunized with native HBsAg in CFA on day 28, and boosted intraperitoneally on day 14. Some animals were then fed PBS (control), or 0.1, 1, or 3 mg of the denatured HBsAg for four consecutive doses every second day. Spleen cells were isolated and cultured with the addition of PBS, or 0.1, 1 or 5 µg of native HBsAg for 3 days. All cultures were pulsed with tritiated thymidine for 18 hours, and the amount of incorporated label was determined by scintillography. As illustrated in FIG. 6, the dissociated HBsAg induced tolerance following oral administration while the mock-dissociated protein did not.

This experiment illustrates that denaturation of the HBsAg resulted in minimally in the loss of the ability to act as a booster immunogen when presented per os, and showed statistically significant immune suppression only when 5 mg of the smallest MW fraction was fed.

Example 6

Figure 8:
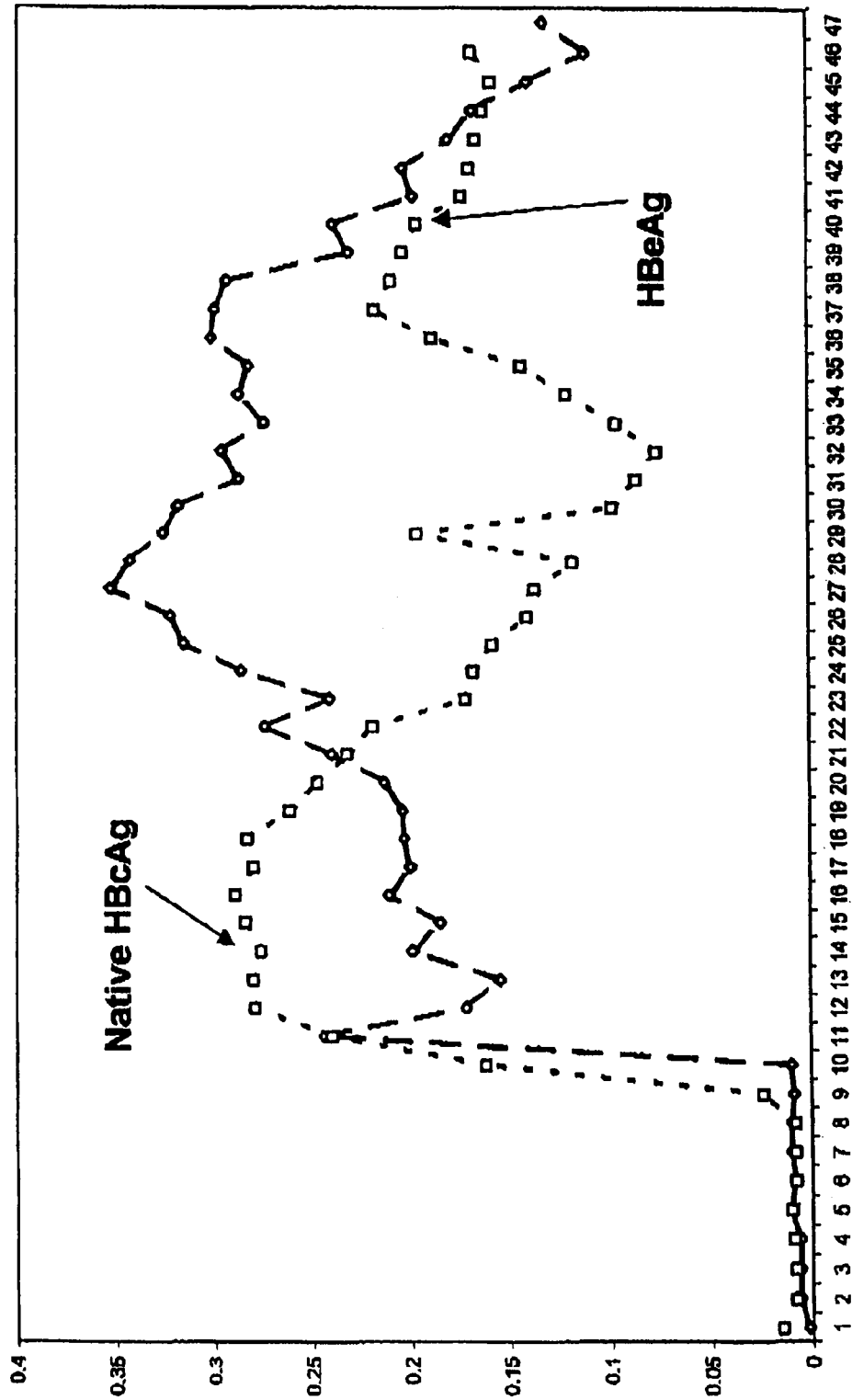
FIG. 8 is a line graph showing the size distribution of ag HBcAg and the local presence of immune reactive ag HBcAg at varying densities (sizes) after fractionation on a sucrose density gradient following isopycnic ultracentrifugation. Ag HBcAg was applied to a Sepharose G-200 column and were fractions collected while monitoring the OD at 280 nm. Each fraction was then tested for the presence of immunoreactive ag HBcAg. Fraction numbers are on the X-axis and $OD_{280\ nm}$ measurements are on the left Y-axis. The OD of the ELISA assay for each fraction is presented on the right Y-axis.

Determination of the Average Aggregate Size Maximally Effective in Inducing Mucosal Tolerance To determine the approximate molecular weight of aggregates present in the three pools, an aliquot of HBsAg was treated as described above, and applied to a Sepharose G200 column. This size filtration resin can resolve molecular weights from approximately 20 kD (approximately 3 HBsAg monomer aggregates) to 200 kD (approximately 200 HBsAg monomer aggregates). The $OD_{280\ nm}$ of the effluent was monitored, and average size of HBsAg aggregates present in the pools calculated. Pool 1 was determined to elute predominantly in the void volume indicating an average size of greater than 2,000 kD. Pool 2 (low mw denatured HBcAg), a fraction determined to have demonstrable but less than maximal effectiveness, had an $M_R$ of 165 kD, or approximately 17 subunits, suggesting that the genetic engineering successfully prevented oligomer formation. FIG. 8 shows that the size of the engineered antigen (HBeAg) was significantly smaller than native as determined by sedimentation on a sucrose density gradient. Pool 3 was composed predominantly of aggregates of between 10 and 3 monomers.

Example 7

Construction Expression, Isolation and Effectiveness of Modified HBcAg

The experiments described above clearly indicate that the ability of an antigen to induce mucosal tolerance depends critically on its physical conformation and thus physical size. Proteins which self-assemble into macromolecular structures such as HBsAg and HBcAg expressed in transgenic systems resulting in pseudovirions and pseudocapsids with multiple-nanometer diameters either fail to induce mucosal tolerance (HBcAg) or stimulate a booster effect in animals previously rendered immune by other means. To establish this principle for an application for treating certain chronic infections as described in U.S. Pat. No. 6,355,348, the gene (residues 1816 through 2454 with modifications) encoding HBcAg (serotype ayw) was modified to a) eliminate its capacity to bind nucleic acids through the protamine domain entailing the arginine rich 5' section of the gene, and b) to minimize the propensity of the protein to self-assemble into pseudocapsids, a property mapped by others to this coding region (Schodel et al., 1993, JBC 268:1332-1337).

Plasmid TKHH2 (Will et. al., 1985, PNAS 82:800-895) containing a tandem head to tail copy of HBV genome was digested with restriction endonucleases to produce the desired coding sequence, and inserted into a pET28A vector system (NovaGen). Following transfection into competent B-21 E. coli, successful transformants were selected by growth on EMB agar containing 50 µg/ml ampicillin. Following dilution in LB medium containing ampicillin, bacteria were re-streaked and a single colony selected for seed-stock expansion. Seed stock was established in 50% glycerol and 50% LB medium stored at –80° C. The amino-terminus of the protein was altered to contain an additional 7 amino acids from the native pre-core sequence to enhance solubility. The carboxy-terminus contains two amino acids (leu, glu) as an artifact of engineering and a 6-histidine tail for protein isolation by nickel affinity. The plasmid engineered for protein expression was sequenced and the DNA sequence was translated into the following amino acid composition. The plasmid DNA sequence had an exact 477 nucleotide overlap with the published DNA of the HBV genome, and when translated to preferred amino acid usage in E. coli, resulted in the following peptide sequence (SEQ ID NO:3):

MQASKLCLGWLWGMDIDPYKEFGATVELLSFLPSDFFPSVRDLLDTAS

ALYREALESPECHSPHHTALRQAILCWGELMTLATWVGVNLEDPASRD

LVVSYVNTNMGLKFRQLLWFHISCLTFGRETVIEYLVSFGVWIRTPPA

YRPPNAPILSTLPETTLEHHHHHH.

This protein differs from naturally occurring HBeAg in that five amino acid residues are uniquely present in the carboxy-terminal region of the construct.

The above protein was expressed and isolated with starter culture is established in LB broth containing both ampicillin and chloramphenoicol. After overnight growth, an aliquot of the culture was used to inoculate a 20 L culture in a Micros 30 fermentor. Once the $OD_{600\ nm}$ of the culture reached 8 (±2), the IPTG concentration was brought to 1 mM for transgene expression induction, which continued for 4 hours. Bacterial cells were pelleted with centrifugation, resuspended in 200 mM Tris, pH 8.0, and disrupted using 4 passes though a micro-fluidizer. The lysate was stored frozen at –80° C. The lysate (100 ml) was then thawed, diluted with 200 ml 50 mM Tris pH 8.0, and centrifuged for 30 minutes at 5000 RPM. The supernatant was removed, and an additional 200 ml 50 mM Tris pH 8.0 was added. The suspension was again centrifuged at 13000 RPM for 30 min, and the supernatant then removed. The pellets were combined and solubilized with 235 ml of 8M urea in 50 mM Tris pH 8.0 with constant mixing at room temperature. After a 30 minute incubation with frequent mixing, the mixture was applied to a 1 cm×100 cm column previously loaded with HISBIND resin (NovaGen) equilibrated with 8 M urea, 50 mM Tris pH 8.0. The flow through fraction was collected, and a wash volume (300 ml) of 8M urea in 50 mM Tris pH 8.0 passed over the column, with 50 ml fractions collected. HBeAg elution was performed by exchanging 8M urea in 50 mM Tris pH 8.0 for 1 M imidazole, eluting the bound product, and collecting 50 ml fractions. Fractions containing ≥90% product as determined by PAGE and western blotting were pooled and dialyzed into PBS. Each fraction of affinity-column eluate was assayed by both PAGE, stained using Coomassie dye or silver-staining techniques, and by western blotting. Densitometric analysis of the resulting gel was performed using each aliquot, and only samples of greater than 90% purity were pooled for subsequent use. Proteins other than transgene-specific bands, as determined by western blot analysis, are believed to be of BL-21 origin.

The relative efficacy of the HBeAg to induce mucosal tolerance in immune mice compared to native HBcAg or ag HBcAg was tested by first immunizing normal CB17 mice of both sexes with sub-q injections of 10 µg of native (non-modified) protein emulsified in CFA. Two weeks later, mice were boosted with intraperitoneal injections of 10 µg of the same antigen. Some mice were treated with injections of PBS/CFA and boosted with PBS to serve as non-immune controls. Selected mice received per os treatments of 0.1, 1 and 5 mg of the modified HBcAg, or doses of native HBcAg or ag HBcAg previously found to be maximally effective. Some mice received PBS per os as appropriate for a total of four treatments applied every second day. Two days following the final treatment, the mice were euthanized, and the isolated spleen cells challenged in culture with antigen in vitro. The responses were quantified by the incorporation of $^3$H-Tdr as described.

Figure 7:
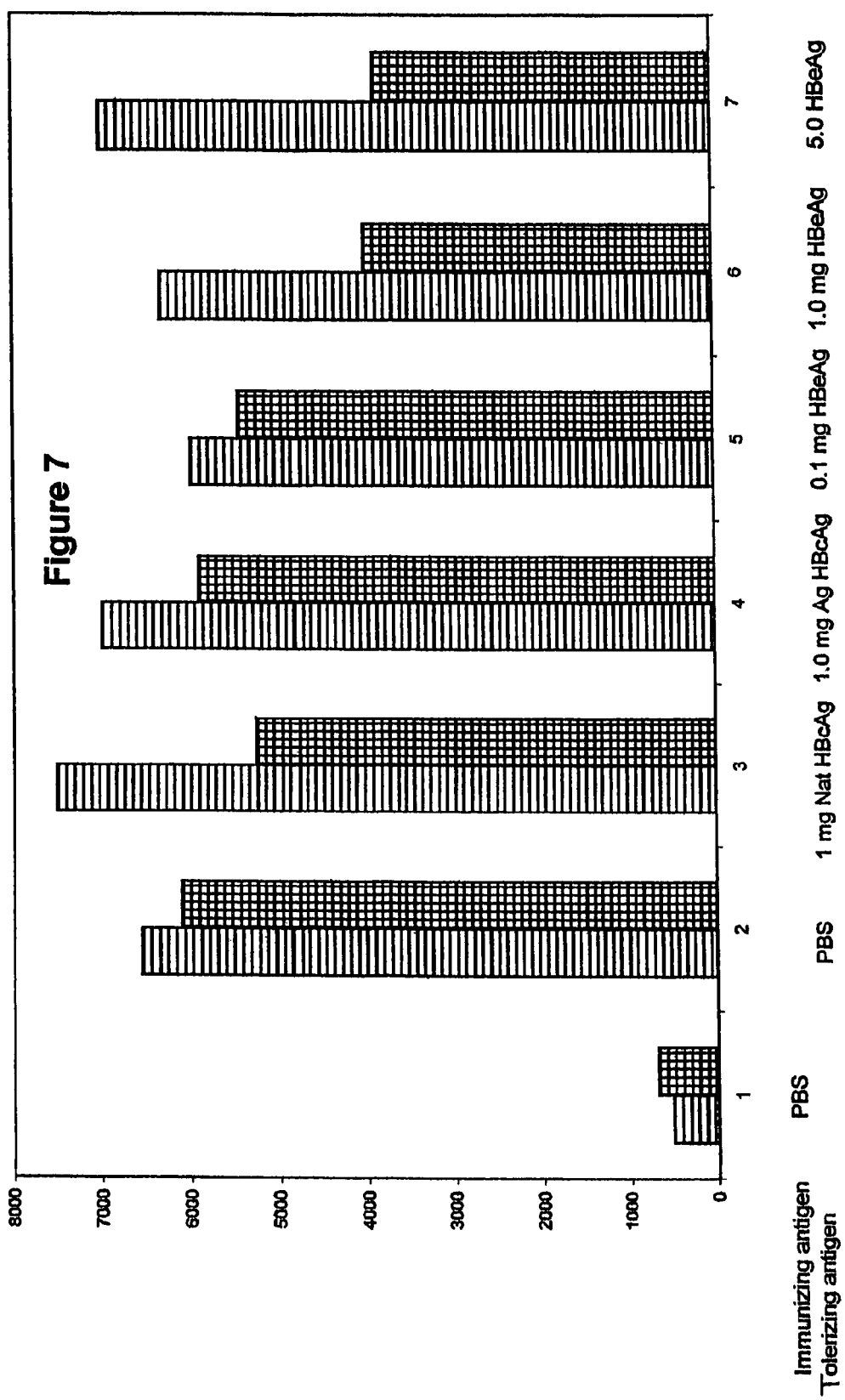
FIG. 7 is a bar graph illustrating that HBeAg is superior to either native HBcAg or aggregated HBcAg as a tolerogen on a per-weight basis. For four treatments every second day, mice were immunized with ag HBcAg, boosted, and then 28 days later, orally tolerized with PBS or the indicated amounts of one of the physical forms of HBcAg explored herein. The left (horizontally striped) bars represent the proliferation response when spleen cells from immune mice challenged with native HBcAg in vitro. The right (vertically striped) bars represent the results of spleen cells collected from immune and orally tolerized mice. Cells were challenged with 5 ug of ag HBcAg per well. The left axis presents the incorporated $^3$H-Tdr as CPM.

FIG. 7 clearly shows that aggregated HBcAg was effective at inducing mucosal tolerance as previously shown. Native HBcAg appeared to be less effective, perhaps due its particulate conformation. Modified HBeAg was significantly more effective than the other two forms of the protein, while HBeAg administered at the same doses induced a significantly greater suppression. The suppression was greater than that observed for pool 2 (low mw denatured HBcAg), suggesting that the genetic engineering successfully prevented oligomers formation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing tolerance to a peptide in a mammal, the method comprising transmucosally administering to the mammal a macromolecular aggregate of the peptide, thereby inducing tolerance to the peptide in the mammal, wherein the macromolecular aggregate comprises less than 21 peptide subunits.

2. A method of inducing tolerance to a peptide in a mammal, the method comprising transmucosally administering to the mammal a macromolecular aggregate of the peptide, thereby inducing tolerance to the peptide in the mammal, wherein the macromolecular aggregate comprises at least one of the members selected from the group consisting of twenty peptide subunits, an aggregate of a molecular weight in excess of 1,000 kD, and a combination of twenty peptide subunits and an aggregate of a molecular weight in excess of 1,000 kD.

3. A method of inducing tolerance to a peptide in a mammal, the method comprising transmucosally administering to the mammal a macromolecular aggregate of the peptide, thereby inducing tolerance to the peptide in the mammal, wherein the macromolecular aggregate is less than 5 nm in diameter.

4. The method of claim 1, 2 or 3, wherein the macromolecular aggregate is resistant to digestive degradation.

5. The method of claim 1, 2 or 3, wherein the macromolecular aggregate is stabilized in aggregate form by chemical treatment.

6. The method of claim 1, 2 or 3, wherein the macromolecular aggregate is stabilized in aggregate form by recombinant protein engineering of the peptide.

7. The method of claim 6, further comprising the stabilization of the macromolecular aggregate in aggregate form by chemical treatment.

8. The method of claim 1, 2 or 3, wherein the peptide comprises a hepatitis B virus protein.

9. The method of claim 8, wherein the peptide is selected from the group consisting of a hepatitis B viral surface protein, a hepatitis B viral nucleocapsid protein, and a hepatitis B viral envelope protein.

10. A method of suppressing an immune response to a peptide in a mammal already immune to said peptide, the method comprising transmucosally administering to the mammal a macromolecular aggregate of the peptide, thereby suppressing an immune response to a peptide in a mammal, wherein the macromolecular aggregate is less than 1 nm in diameter.

11. A method of suppressing an immune response to a peptide in a mammal already immune to said peptide, the method comprising transmucosally administering to the mammal a macromolecular aggregate of the peptide, thereby suppressing an immune response to a peptide in a mammal, wherein the macromolecular aggregate comprises 10 or less peptide subunits.

12. A method of suppressing an immune response to a peptide in a mammal already immune to said peptide, the method comprising transmucosally administering to the mammal a macromolecular aggregate of the peptide, thereby suppressing an immune response to a peptide in a mammal, wherein the macromolecular aggregate has a molecular weight of 1,000 kD or less.

13. The method of claim 10, 11 or 12, wherein the macromolecular aggregate is resistant to digestive degradation.

14. The method of claim 10, 11 or 12, further comprising stabilization of the macromolecular aggregate in aggregate form by chemical treatment.

15. The method of claim 10, 11 or 12, further comprising stabilization of the macromolecular aggregate in aggregate form by recombinant protein engineering of the peptide.

16. The method of claim 15, further comprising stabilization of the macromolecular aggregate in aggregate form by chemical treatment.

17. The method of claim 10, 11 or 12, wherein the peptide comprises a hepatitis B virus protein.

18. The method of claim 17, wherein the peptide is selected from the group consisting of a hepatitis B viral surface protein, a hepatitis B viral nucleocapsid protein, and a hepatitis B viral envelope protein.

19. The method of claim 1, 2 or 3, wherein the peptide comprises an antigen that is an immune target attacked by the mammal's immune system in an autoimmune disease.

20. The method of claim 10, 11 or 12, wherein the peptide comprises an antigen that is an immune target attacked by the mammal's immune system in an autoimmune disease.

21. The method of claim 1, 2 or 3, wherein the peptide is administered orally.

22. The method of claim 10, 11 or 12, wherein the peptide is administered orally.

* * * * *